(12) United States Patent
Lyssikatos et al.

(10) Patent No.: US 6,586,447 B1
(45) Date of Patent: Jul. 1, 2003

(54) 3,3-DISUBSTITUTED-OXINDOLE DERIVATIVES USEFUL AS ANTICANCER AGENTS

(75) Inventors: Joseph Peter Lyssikatos, Gales Ferry, CT (US); Bingwei Vera Yang, Waterford, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/539,930

(22) Filed: Mar. 31, 2000

Related U.S. Application Data
(60) Provisional application No. 60/127,340, filed on Apr. 1, 1999.

(51) Int. Cl.[7] ............... A61K 31/4725; A61K 31/4178; A61P 35/00; C07D 401/14; C07D 403/14
(52) U.S. Cl. .............. 514/309; 514/314; 514/333; 514/339; 514/397; 546/142; 546/152; 546/256; 546/275.4; 548/312.1
(58) Field of Search .................. 546/142, 152, 546/256, 275.4; 548/312.1; 514/309, 314, 333, 339, 397

(56) References Cited

U.S. PATENT DOCUMENTS
5,948,781 A * 9/1999 Lyssikatos .................. 514/256

OTHER PUBLICATIONS
Khosravi–Far R et al. Cell Growth & Differentiation. vol. 3, pp. 461–469. Jul. 1992.*
Mallam AK et al. J. Med. Chem. vol. 41, pp. 877–893. 1998.*
Graham SL. Exp. Opin. Ther. Patents. 5(12), pp. 1269–1285. 1995.*

* cited by examiner

*Primary Examiner*—Evelyn Mei Huang
(74) *Attorney, Agent, or Firm*—Peter C. Richardson; Paul H. Ginsburg; Krishna G. Banerjee

(57) ABSTRACT

The present invention relates to compounds of formula 1

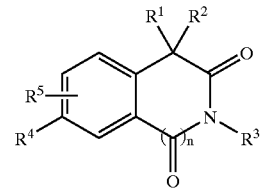

and to pharmaceutically acceptable salts, prodrugs, and solvates thereof, wherein n is 0 or 1 and $R^1$, $R^2$, $R^3$, $R^4$, and $R^5$ are as defined herein. The above compounds of formula 1 are useful in the treatment of hyperproliferative disorders, such as cancer, in mammals. The invention also relates to pharmaceutical compositions containing the compounds of formula 1, to methods of inhibiting abnormal cell growth, including cancer, in a mammal by administering the compounds of formula 1 to a mammal requiring such treatment, and to methods of preparing compounds of formula 1.

21 Claims, No Drawings

3,3-DISUBSTITUTED-OXINDOLE DERIVATIVES USEFUL AS ANTICANCER AGENTS

This Application claims priority from U.S. provisional Application Ser. No. 60/127,340, filed Apr. 1, 1999.

BACKGROUND OF THE INVENTION

This invention relates to a series of 3,3-disubstituted-oxindole derivatives that are useful in the treatment of hyperproliferative diseases, such as cancers, in mammals. This invention also relates to a method of using such compounds in the treatment of hyperproliferative diseases in mammals, especially humans, to pharmaceutical compositions containing such compounds, and to methods of preparing such compounds. Oxindole derivatives alleged to have CNS activity have been described in EP 0311010 B1 and EP 241 006.

Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer.

To become functional, the precursor of the Ras oncoprotein must undergo farnesylation of the cysteine residue located in a carboxyl-terminal tetrapeptide. Inhibitors of the enzyme that catalyzes this modification, farnesyl protein transferase, have therefore been suggested as agents to combat tumors in which Ras contributes to transformation. Mutated, oncogenic forms of Ras are frequently found in many human cancers, most notably in more than 50% of colon and 90% pancreatic carcinomas (Kohl et al., *Science*, Vol. 260, 1834 to 1837, 1993). The compounds of the present invention exhibit activity as inhibitors of the enzyme farnesyl protein transferase and are therefore believed to be useful as anti-cancer and anti-tumor agents. Further, the compounds of the present invention may be active against any tumors that proliferate by virtue of farnesyl protein transferase.

SUMMARY OF THE INVENTION

The present invention relates to compounds of formula 1

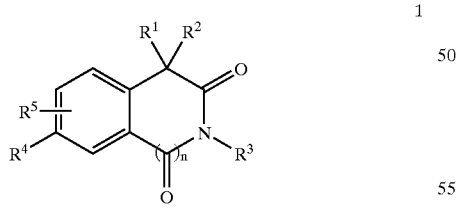

1 and to pharmaceutically acceptable salts, prodrugs, and solvates thereof wherein:

n is 0 or 1;

$R^1$ is $C_1$–$C_3$ alkylpyridyl or $C_1$–$C_3$ alkylimidazolyl;

$R^2$ is selected from the group consisting of $C_1$–$C_{10}$ alkyl, $C_2$–$C_{10}$ alkenyl, $C_2$–$C_{10}$ alkynyl, —$(CH_2)_p(C_6$–$C_{10}$ aryl), and —$(CH_2)_p$(4–10 membered unsaturated heterocyclyl), wherein p is an integer from 0 through 3, and wherein any of said $R^1$ and $R^2$ groups are optionally substituted with 1 to 3 $R^6$ groups;

$R^3$ is —$(CH_2)_m$(1- or 2-adamantyl), $C_1$–$C_{10}$ alkyl, $C_2$–$C_{10}$ alkenyl, $C_2$–$C_{10}$ alkynyl, —$(CH_2)_m(C_6$–$C_{10}$ aryl),

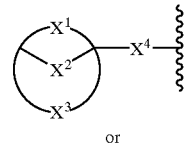

(1a)

or

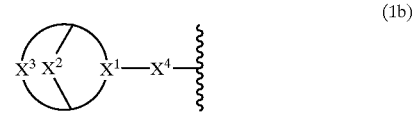

(1b)

$X^1$, $X^2$, and $X^3$ are each independently $C_1$–$C_7$ alkylene optionally containing 1 or 2 carbon-carbon double bonds, $X^4$ is a bond or $C_{1-7}$ alkylene optionally containing 1 or 2 carbon-carbon double or triple bonds, and, in formula (1b), the $X^4$ moiety is attached to the $X^1$ moiety at any available carbon in the $X^1$ moiety, and each of the foregoing $R^3$ groups are optionally substituted with an $R^5$ group and optionally with 1 to 4 $R^6$ groups, or $R^3$ is —$(CH_2)_tSO_2R^9$, —$(CH_2)_tC(O)R^9$, or —$(CH_2)_m$ (4–10 membered heterocyclyl) optionally substituted with 1 to 5 $R^6$ groups;

m, in the aforementioned $R^3$ groups, is independently an integer from 0 through 6 and t is independently an integer from 1 through 5;

$R^4$ is $C_6$–$C_{10}$ aryl or 4–10 membered heterocyclyl, each of said $R^4$ groups being optionally substituted by 1 to 3 $R^6$ groups;

each $R^5$ is independently selected from halo, $C_1$–$C_6$ alkyl optionally substituted by 1 to 3 halo, nitro, cyano, —$OR^9$, —$C(O)R^9$, $SR^9$, —$SO_2R^9$, —$SO_3H$, —$S(O)R^9$, —$NR^7R^8$, —$CH$=$NOR^7$, —$C(O)OR^9$, —$OC(O)R^9$, —$SO_2NR^9R^8$, —$C(O)NR^9R^8$, —$NR^8C(O)R^9$, —$OC(O)NR^9R^8$, —$C(O)ONR^7R^9$, —$NR^8C(O)NR^9R^8$, —$NR^8C(O)O(C_1$–$C_4$ alkyl), —$C(NR^8)NR^9R^8$, —$C(NCN)NR^9R^8$, —$C(NCN)S(C_1$–$C_4$ alkyl or $C_1$–$C_4$ haloalkyl), —$NR^8C(NCN)S(C_1$–$C_4$ alkyl or $C_1$–$C_4$ haloalkyl), —$NR^8C(NCN)NR^7R^8$, —$NR^8SO_2(C_1$–$C_4$ alkyl or $C_1$–$C_4$ haloalkyl), —$NR^8C(O)C(O)R^8$, —$NR^8C(O)C(O)NR^9R^8$, —$P(O)(OR^7)_2$, and —$(CH_2)_q$ (4–10 membered heterocyclyl), each q is independently an integer from 0 through 3, and the alkyl and heterocyclyl moieties of the foregoing $R^5$ groups are optionally substituted by 1 to 3 $R^{10}$ groups;

each $R^6$ is independently selected from $R^5$, $C_2$–$C_{10}$ alkenyl, $C_2$–$C_{10}$ alkynyl and —$(CH_2)_t(C_6$–$C_{10}$ aryl) optionally substituted with 1 to 3 $R^{10}$ groups, t is an integer from 0 through 3;

each $R^7$ is independently hydrogen or $C_1$–$C_4$ alkyl optionally substituted by 1 to 3 halo;

each $R^8$ is independently $R^7$ or —$OR^7$;

each $R^9$ is independently selected from hydrogen, $C_1$–$C_6$ alkyl, —$(CH_2)_q(C_6$–$C_{10}$ aryl) and —$(CH_2)_q$ (4–10 membered heterocyclyl), said $R^9$ groups, except H, are optionally substituted with 1 to 3 $R^{10}$ groups, and each q is independently an integer from 0 through 3; and, each $R^{10}$ is independently selected from halo, nitro, cyano, $C_1$–$C_6$ alkyl, $C_1$–$C_6$ haloalkyl, $C_1$–$C_6$ haloalkoxy, —$C(O)O(C_1$–$C_6$ alkyl), and $C_6$–$C_{10}$ aryl.

Preferably, in the compounds of formula 1, each p integer in $R^2$ is an integer independently selected from 0 to 3, more preferably an integer independently selected from 1 to 3, 1 being most preferred.

Preferred compounds of formula 1 include those wherein one or both of $R^1$ and $R^2$ is —$(CH_2)_p$(4–10 membered unsaturated heterocyclyl) optionally substituted with 1 to 3 $R^6$ groups, more preferably —$(CH_2)_p$(5 or 6 membered unsaturated heterocyclyl). Preferably, each heterocyclyl of $R^1$ and $R^2$ is independently imidazolyl or pyridinyl. In different embodiments, one or both $R^1$ and $R^2$ is 2-, 3-, or 4-pyridinylmethyl; preferably, one or both of $R^1$ and $R^2$ is 4-pyridinylmethyl. In other embodiments, $R^1$ and $R^2$ are each independently imidazol-1-ylmethyl, imidazol-2-ylmethyl, or imidazol-4-ylmethyl, optionally substituted with 1 to 3 $R^6$ groups; preferably, $R^1$ and $R^2$ are both imidazol-4-ylmethyl, each optionally substituted with 1 to 3 $R^6$ groups. When only one of $R^1$ and $R^2$ is a —$(CH_2)_p$(4–10 membered unsaturated heterocyclyl) optionally substituted with 1 to 3 $R^6$ groups, the other of $R^1$ or $R^2$ is a $C_1$–$C_{10}$ alkyl substituted by one $R^6$ group, wherein the Re group is preferably, —$SR^9$; preferably, both of $R^1$ or $R^2$ is imidazolyl or pyridinyl, more preferably imidazol-1-ylmethyl, imidazol-2-ylmethyl, imidazol-4-ylmethyl or 4-pyridinylmethyl.

Preferred compounds of formula 1 include those wherein $R^3$ is —$(CH_2)_m$(1- or 2-adamantyl) or —$(CH_2)_m$($C_6$–$C_{10}$ aryl), wherein the aryl group is optionally substituted with 1 to 5 $R^6$ groups, preferably wherein m is an integer 1. Preferably the aryl group is phenyl or naphthyl and $R^6$ is $R^5$, wherein $R^5$ is —$SO_2R^9$, —$SO_2NR^9R^8$, or —$C(O)OR^9$, preferably, —$SO_2NR^9R^8$.

Other preferred compounds of formula 1 include those wherein $R^4$ is $C_6$–$C_{10}$ aryl substituted by $R^6$, preferably, wherein the $R^6$ is cyano. Other preferred compounds of formula 1 include those wherein $R^4$ is $C_6$–$C_{10}$ aryl substituted by $R^6$, wherein the $R^6$ is preferably halo or formyl, provided that when the $R^6$ is bromo, then $R^3$ is substituted by $R^5$, wherein $R^5$ is sulfonamide.

Specific preferred compounds include the following:

4-[6-(4-Cyano-phenyl)-3,3-bis-(1H-imidazol-4-ylmethyl)-2-oxo-2,3-dihydro-indol-1-ylmethyl]-N,N-dimethyl-benzenesulfonamide;

4-[3,3-Bis-(3H-imidazol-4-ylmethyl)-1-naphthalen-1-ylmethyl-2-oxo-2,3-dihydro-1H-indol-6-yl]-benzonitrile;

4-[1-Adamantan-1-ylmethyl-3-(1H-imidazol-4-ylmethyl)-3-(3H-imidazol-4-ylmethyl)-2-oxo-2,3-dihydro-1H-indol-6-yl]-benzonitrile;

4-[3-(1H-imidazol-4-ylmethyl)-3-(3H-imidazol-4-ylmethyl)-2-oxo-1-quinolin-4-ylmethyl-2,3-dihydro-1H-indol-6-yl]-benzonitrile;

4-[6-(4-Formyl-phenyl)-2-oxo-3,3-bis-pyridin-4-ylmethyl-2,3-dihydro-indol-1-ylmethyl]-N,N-dimethyl-benzenesulfonamide;

4-[6-(4-Cyano-phenyl)-2-oxo-3,3-bis-pyridin-4-ylmethyl-2,3-dihydro-indol-1-ylmethyl]-N,N-dimethyl-benzenesulfonamide;

4-(1-Naphthalen-1-ylmethyl-2-oxo-3,3-bis-pyridin-4-ylmethyl-2,3-dihydro-1H-indol-6-yl)-benzonitrile;

4-(2-Oxo-3,3-bis-pyridin-4-ylmethyl-1-quinolin-4-ylmethyl-2,3-dihydro-1H-indol-6-yl)-benzonitrile;

4-[1-Adamantan-1-ylmethyl-3,3-bis-(3-methyl-3H-imidazol-4-ylmethyl)-2-oxo-2,3-dihydro-1H-indol-6-yl]-benzonitrile;

4-(7-Methyl-1-naphthalen-2-ylmethyl-2-oxo-3,3-bis-pyridin-4-ylmethyl-2,3-dihydro-1H-indol-6-yl)-benzonitrile;

4-(7-Methyl-1-naphthalen-1-ylmethyl-2-oxo-3,3-bis-pyridin-4-ylmethyl-2,3-dihydro-1H-indol-6-yl)-benzonitrile;

4-[6-(4-Cyano-phenyl)-7-methyl-2-oxo-3,3-bis-pyridin-4-ylmethyl-2,3-dihydro-indol-1-ylmethyl]-N,N-dimethyl-benzenesulfonamide;

4-[7-Methyl-1-naphthalen-1-ylmethyl-2-oxo-3-(1H-pyrazol-4-ylmethyl)-3-pyridin-4-ylmethyl-2,3-dihydro-1H-indol-6-yl]-benzonitrile;

4-[3,3-Bis-(1H-imidazol-4-ylmethyl)-7-methyl-1-naphthalen-1-ylmethyl-2-oxo-2,3-dihydro-1H-indol-6-yl]-benzonitrile;

4-[7-Methyl-3,3-bis-(5-methyl-1H-imidazol-4-ylmethyl)-1-naphthalen-1-ylmethyl-2-oxo-2,3-dihydro-1H-indol-6-yl]-benzonitrile;

4-(2-Naphthalen-1-ylmethyl-1,3-dioxo-4,4-bis-pyridin-4-ylmethyl-1,2,3,4-tetrahydro-isoquinolin-7-yl)-benzonitrile; and 4-{1,3-Dioxo-4,4-bis-pyridin-4-ylmethyl-2-[1-(thiophene-2-sulfonyl)-pyrrolidin-3-yl]-1,2,3,4-tetrahydro-isoquinolin-7-yl}-benzonitrile.

and the pharmaceutically acceptable salts, prodrugs, and solvates of the foregoing compounds, as well as stereoisomers of the foregoing compounds.

This invention also relates to a method for the treatment of abnormal cell growth in a mammal, including a human, comprising administering to said mammal an amount of a compound of the formula 1, as defined above, or a pharmaceutically acceptable salt, prodrug or solvate thereof, that is effective in inhibiting farnesyl protein transferase. In one embodiment of this method, the abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said method, said abnormal cell growth is a benign proliferative disease, including, but not limited to, psoriasis, benign prostatic hypertrophy or restinosis.

This invention also relates to a method for the treatment of abnormal cell growth in a mammal, including a human, comprising administering to said mammal an amount of a compound of the formula 1, as defined above, or a pharmaceutically acceptable salt, prodrug, or solvate thereof, that is effective in treating abnormal cell growth.

This invention also relates to a method for the treatment of abnormal cell growth in a mammal which comprises administering to said mammal a therapeutically effective amount of a compound of formula 1, or a pharmaceutically acceptable salt, prodrug, or solvate thereof, in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

The present invention also relates to a method for the treatment of an infection in a mammal, including a human, that is facilitated by farnesyl protein transferase, such as hepatitis delta virus or malaria, which comprises administering to said mammal a therapeutically effective amount of a compound of formula 1 or a pharmaceutically acceptable salt, prodrug, or solvate thereof.

This invention also relates to a pharmaceutical composition for the treatment of abnormal cell growth in a mammal, including a human, comprising an amount of a compound of the formula 1, as defined above, or a pharmaceutically acceptable salt, prodrug, or solvate thereof, that is effective in inhibiting farnesyl protein transferase, and a pharmaceutically acceptable carrier. In one embodiment of said composition, said abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft issue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said pharmaceutical composition, said abnormal cell growth is a benign proliferative disease, including, but not limited to, psoriasis, benign prostatic hypertrophy or restinosis.

This invention also relates to a pharmaceutical composition for the treatment of abnormal cell growth in a mammal, including a human, comprising an amount of a compound of the formula 1, as defined above, or a pharmaceutically acceptable salt, prodrug, or solvate thereof, that is effective in treating abnormal cell growth, and a pharmaceutically acceptable carrier.

The invention also relates to a pharmaceutical composition for the treatment of abnormal cell growth in a mammal, including a human, which comprises a therapeutically effective amount of a compound of formula 1, as defined above, or a pharmaceutically acceptable salt, prodrug, or solvate thereof, in combination with a pharmaceutically acceptable carrier and an anti-tumor agent selected from the group consisting of mitotic inhibitors, alkylating agents, antimetabolites, intercalating antibiotics, growth factor inhibitors, cell cycle inhibitors, enzymes, topoisomerase inhibitors, biological response modifiers, anti-hormones, and anti-androgens.

This invention also relates to a pharmaceutical composition for the treatment of an infection in a mammal, including a human, that is facilitated by farnesyl protein transferase, such as malaria or hepatitis delta virus, comprising an amount of a compound of the formula 1, as defined above, or a pharmaceutically acceptable salt, prodrug, or solvate thereof, that is effective in treating abnormal cell growth, and a pharmaceutically acceptable carrier.

"Abnormal cell growth", as used herein, unless otherwise indicated, refers to cell growth that is independent of normal regulatory mechanisms (e.g., loss of contact inhibition). This includes the abnormal growth of (1) tumor cells (tumors) expressing an activated Ras oncogene; (2) tumor cells in which the Ras protein is activated as a result of oncogenic mutation in another gene; (3) benign and malignant cells of other proliferative diseases in which aberrant Ras activation occurs; and (4) any tumors that proliferate by virtue of farnesyl protein transferase.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

The term "halo", as used herein, unless otherwise indicated, means fluoro, chloro, bromo or iodo. Preferred halo groups are fluoro, chloro and bromo.

The term "alkyl", as used herein, unless otherwise indicated, includes saturated monovalent hydrocarbon radicals having straight or branched moieties.

The term "cycloalkyl", as used herein, unless otherwise indicated, includes cyclic alkyl moieties wherein alkyl is as defined above.

The term "alkenyl", as used herein, unless otherwise indicated, includes alkyl moieties having at least one carbon-carbon double bond wherein alkyl is as defined above.

The term "alkynyl", as used herein, unless otherwise indicated, includes alkyl moieties having at least one carbon-carbon triple bond wherein alkyl is as defined above.

The term "alkylene", as used herein, unless otherwise indicated, means divalent hydrocarbon radicals which are straight or branched.

The term "alkoxy", as used herein, unless otherwise indicated, includes O-alkyl groups wherein alkyl is as defined above.

The term "aryl", as used herein, unless otherwise indicated, includes an organic radical derived from an aromatic hydrocarbon by removal of one hydrogen, such as phenyl or naphthyl.

The term "4–10 membered heterocyclic", as used herein, unless otherwise indicated, includes aromatic and non-aromatic heterocyclic groups containing one or more heteroatoms, generally 1 to 4 heteroatoms, each selected from O, S and N, wherein each heterocyclic group has from 4–10 atoms in its ring system. Non-aromatic heterocyclic groups include groups having only 4 atoms in their ring system, but aromatic heterocyclic groups must have at least 5 atoms in their ring system. The heterocyclic groups include benzo-fused ring systems and ring systems substituted with one or more oxo moieties. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached).

The term "pharmaceutically acceptable salt(s)", as used herein, unless otherwise indicated, includes salts of acidic or basic groups that may be present in the compounds of formula 1. The compounds of the present invention that are basic in nature are capable of forming a wide variety of salts with various inorganic and organic acids. The acids that may be used to prepare pharmaceutically acceptable acid addition salts of such basic compounds are those that form non-toxic acid addition salts, L!L., salts containing pharmacologically acceptable anions, such as the hydrochloride, hydrobromide, hydroiodide, nitrate, sulfate, bisulfate, phosphate, acid phosphate, hydrogen phosphate, dihydrogen phosphate, isonicotinate, acetate, lactate, sailcylate, citrate, acid citrate, tartrate, pantothenate, bitartrate, ascorbate, succinate, maleate, gentisinate, fumarate, gluconate, glucuronate, saccharate, formate, benzoate, glutamaite, methanesulfonate (meslyate), ethanesulfonate, benzenesulfanate, p-toluenesulfonate (tosylate), mandelate, and pamoate i.e., 1,1'-methylene-bis-(2-hydroxy-3-naphthoate) salts. The compounds of the present invention that include a basic moiety, such as an amino group, may form pharmaceutically acceptable salts with various amino acids, in addition to the acids mentioned above.

Those compounds of the present invention that are acidic in nature are capable of forming base salts with various pharmacologically acceptable cations. Examples of such salts include the alkali metal or alkaline earth metal salts and, particularly, the calcium, magnesium, sodium and potassium salts of the compounds of the present invention.

Certain compounds of formula 1 may have asymmetric centers and therefore exist in different enantiomeric and diastereomeric forms. All optical isomers and stereoisomers of the compounds of formula 1, and mixtures thereof, and all pharmaceutical compositions and methods of treatment that may employ or contain them, are considered to be within the scope of the invention. With respect to the compounds of formula 1, the invention includes the use of a racemate, one or more enantiomeric forms, one or more diastereomeric forms, or mixtures thereof. In particular, the carbon to which the $R^1$ and $R^2$ groups are attached represents a potential chiral center; the present invention encompasses all stereoisomers based on this chiral center. The compounds of formula 1 may also exist as tautomers. This invention relates to the use of all such tautomers and mixtures thereof. Certain compounds of formula 1 may also include oxime moieties, such as where $R^5$ is —CH=NOR$^7$, that exist in E or Z configurations. The present invention includes racemic mixtures of compounds of formula 1 that include such oxime moieties or specific E or Z isomers of such compounds.

This invention also includes isotopically-labelled compounds, and the pharmaceutically acceptable salts thereof, which are identical to those recited in formula 1, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O $^{17}$O, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of formula 1 of this invention and prodrugs thereof can generally be prepared by carrying out the procedures disclosed in the Schemes and/or in the Examples and Preparations below, by substituting a readily available isotopically labelled reagent for a non-isotopically labelled reagent.

This invention also encompasses pharmaceutical compositions containing and methods of treating hyperproliferative diseases through administering prodrugs of compounds of the formula 1. Compounds of formula 1 having free amino, amido, hydroxy, or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula 1. The amino acid residues include but are not limited to the 20 naturally occurring amino acids commonly designated by three letter symbols and also includes 4-hydroxyproline, hydroxylysine, demosine, isodemosime, 3-methylhistidine, norvalin, beta-alanine, gamma-aminobutyric acid, citrulline homocysteine, homoserine, ornithine and methionine sulfone.

Additional types of prodrugs, are also encompassed. For instance, free carboxyl groups can be derivatized as amides or alkyl esters. The amide and ester moieties may incorporate groups including but not limited to ether, amine and carboxylic acid functionalities. Free hydroxy groups may be derivatized using groups including but not limited to hemisuccinates, phosphate esters, dimethylaminoacetates, and phosphoryloxymethyloxycarbonyls, as outlined in D. Fleisher, R. Bang, B. H. Stewart, *Advanced Drug Delivery Reviews* 19, p. 115 (1996). Carbamate prodrugs of hydroxy and amino groups are also included, as are carbonate prodrugs and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in R. P. Robinson et al., *J. Med. Chem.* 39, p. 10 (1998). Introduction of prodrug side chains that can be carried out on the hydroxy groups of the compounds of formula 1. For instance, silylation, acylation, alkylation, etc. can be carried out on hydroxy groups of the compounds of formula 1. Selective introduction of prodrug side chains can be carried out on the compounds of formula 1 having more that one protectible group. For example, derivatization of one hydroxy group of a polyhydroxylated compound of formula 1 may be carried out.

DETAILED DESCRIPTION OF THE INVENTION

The compounds of formula 1 may be prepared as described below.

With reference to Scheme 1 below, the compounds of formula 1, wherein the $R^1$ and $R^2$ substituents are the same and are designated by R, may be prepared by alkylating an intermediate oxindole of formula 2, according to methods familiar to those skilled in the art, such as by stirring the intermediate of formula 2 in the presence of a base and an appropriate alkylating agent, such as R—Z, wherein Z is a leaving group, such as chloro in an appropriate solvent. An appropriate base is, for example, potassium hexamethyldisilazide. An appropriate solvent is, for example, tetrahydofuran.

Scheme 1

With reference to Scheme 2 below, the compounds of formula 1, may be prepared by coupling a compound of formula 3, wherein W is an appropriate leaving group, such as halo with a compound of the formula $ZR^4$, wherein $R^4$ is as defined above and Z is an appropriate leaving group, such as —B(OH)$_2$. Said reaction requires the presence of a coupling reagent. Coupling reagents familiar to those skilled in the art include metallic and organometallic reagents. An example of an organometallic reagent is tetrakis(triphenylphosphine)palladium (0), which may be used in the presence of an appropriate solvent, such as toluene/ethanol, and the presence of an aqueous base at a temperature ranging from room temperature to 120° C., preferably from about 80 to 100° C.

Scheme 2

With reference to Scheme 3 below, compounds of formula 1 can be prepared by reacting an intermediate of formula 4 with an appropriate reducing agent, for example NaBH$_4$ in an appropriate solvent(s) such as methanol (MeOH) and tetrahydrofuran (THF). Reaction of the resulting intermediate with a suitable alkylating agent, such as $R^2W$, wherein $R^2$ is as defined above and W is an appropriate leaving group, such as halo. Said reaction requires the presence of a base, such as aqueous KOH. The scheme 3 method is particularly useful for compounds of formula 1 wherein $R^1$ is different than $R^2$.

Scheme 3

Appropriate substituents, such as free nitrogen atoms, of the compounds of formula 1 may be protected with an optional protective group. These protective groups can be removed after the reactions or transformations described above. For example, in the imidazole moiety of a $R^1$ group, a free nitrogen atom may be protected with a triphenylmethyl (trityl) group, which may be removed by stirring in the presence of trifluoroacetic acid (TFA) and triethylsilane.

The substituents of the compounds of formula 1 may be converted to other substituents falling within the scope of formula 1 via reactions or functional group transformations familiar to those skilled in the art. A number of such transformations are already described above. For example, an aldehyde functional group may be transformed into a cyano functional group by methods known to those skilled in the art, such as reacting the compound of formula 1 with hydroxylamine hydrochloride in an appropriate solvent such as a mixture of dichloromethane (DCM) and an alcohol, such as ethanol, isolating a product, and then stirring the product in the presence of triethylamine and p-toluenesulphonyl chloride.

Other examples are hydrolysis of carboxylic esters to the corresponding carboxylic acid or alcohol; hydrolysis of amides to the corresponding carboxylic acids or amines; hydrolysis of nitriles to the corresponding amides; amino groups on imidazole or phenyl moieties may be replaced by hydrogen by diazotation reactions familiar to those skilled in the art, and subsequent replacement of the diazo-group by hydrogen; alcohols may be converted into esters and ethers; primary amines may be converted into secondary or tertiary amines; double bonds may be hydrogenated to the corresponding single bond.

With reference to Scheme 4 below, the compound of formula 5, wherein W is an appropriate leaving group, such as halo, can be reacted to add an $R^4$ group, wherein $R^4$ is an aryl group or a heterocyclic aryl group and using coupling reagents that are known to those of skill in the art, such as palladium catalysis (with a palladium reagent, such as tetrakis(triphenylphosphine)palladium(0)) in the presence of a coupling partner of formula $ZR^4$, wherein Z is an appropriate coupling group, such as —B(OH)$_2$.

Scheme 4

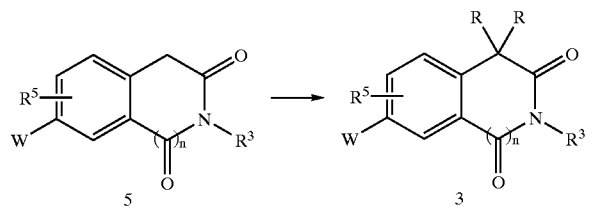

With reference to Scheme 5 below, compounds of formula 3, wherein the $R^1$ and $R^2$ substituents are the same and are designated by R, may be prepared as described above in Scheme 1 for the preparation of a compound of formula 1, by alkylating a compound of formula 5, according to methods familiar to those skilled in the art, such as by stirring the intermediate of formula 6 in the presence of a base and an alkylating agent in an appropriate solvent. For example, an appropriate base is potassium hexamethyldisilazide; an appropriate solvent is, for example, tetrahydofuran; an appropriate alkylating agent is R—Z, wherein Z is a leaving group, such as chloro.

Scheme 5

With reference to Scheme 6 below, the compound of formula 7 may be reacted in the presence of an acid, such as trifluoroacetic acid (TFA) to form a compound of formula 5a, which are intermediates of compounds of formula 5, wherein n is 0. The compound of formula 7 may be prepared by cyclizing a compound of formula 6 in the presence of an acylating agent, such a triphosgene, in an appropriate solvent, such as DCM, and in the presence of a base, such as diisopropylethyl amine, and optionally in the presence of a hindered base, such as 1,8-diazabicyclo[5.4.0]undec-7-ene (DBU). The resulting compound of formula 7, wherein $R^3$ is hydrogen, may be converted to compounds of formula 7, wherein $R^3$ is other than hydrogen as defined above, using procedures familiar to those skilled in the art.

Scheme 6

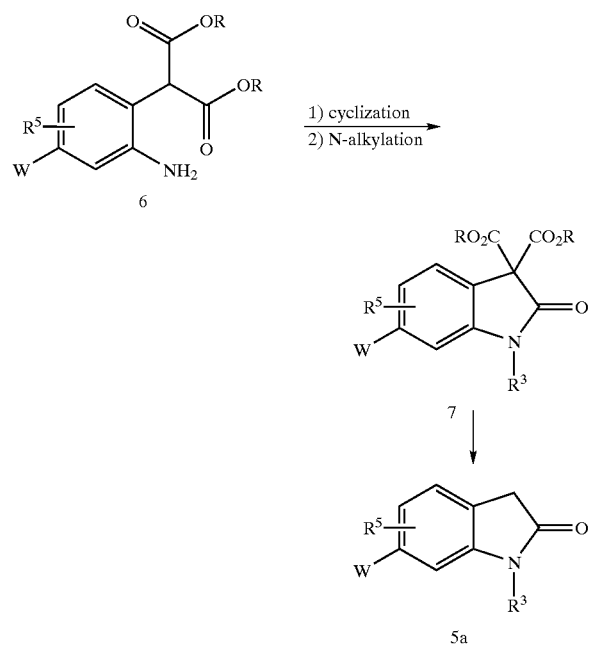

With reference to Scheme 7 below, compounds of formula 3a, which are intermediates of formula 3, wherein n is 0, may be prepared by reducing a compound of formula 11, according to methods familiar to those skilled in the art, such as reacting a compound of formula 11 in the presence of an appropriate reducing agent, such as a hydride reducing agent (such as sodium borohydride), in an appropriate solvent, such as a mixture of tetrahydrofuran and an alcohol, such as methanol (converting the alkenyl-R substituent into either a $R^1$ or a $R^2$ group), and then reacting the reduction product with a reagent of formula RZ, wherein Z is an appropriate leaving group and R is either $R^1$ or $R^2$, under appropriate conditions. Compounds of formula 11 may be prepared by reacting a compound of formula 10 with a reagent of formula H—$R^1$ or H—$R^2$, in the presence of suitable reagent(s), such as acetic acid and acetic anhydride. Compounds of formula 10 may be prepared by reacting a compound of formula 9 under conditions that are familiar to those skilled in the art, such as in the presence of sulfuric acid. Compounds of formula 9, wherein $R^3$ is hydrogen, may be prepared by reacting a compound of formula 8 with ethylene glycol in the presence of an acid, such as p-toluenesulfonic acid, and an appropriate solvent, such as benzene, at reflux temperatures with the removal of water. The resulting compound of formula 9, wherein $R^3$ is hydrogen, may be converted to compounds of formula 9, wherein $R^3$ is other than hydrogen as defined above, using procedures familiar to those skilled in the art.

Compounds of formula 9 may be protected with a protecting group other than dioxolane group used in the methods of Scheme 5. These protecting groups are familiar to those skilled in the art. When the compounds of formula 9 are protected with a protecting group other than dioxolane, those compounds may be converted to compounds of formula 10 according to methods familiar to those skilled in the art.

Scheme 7

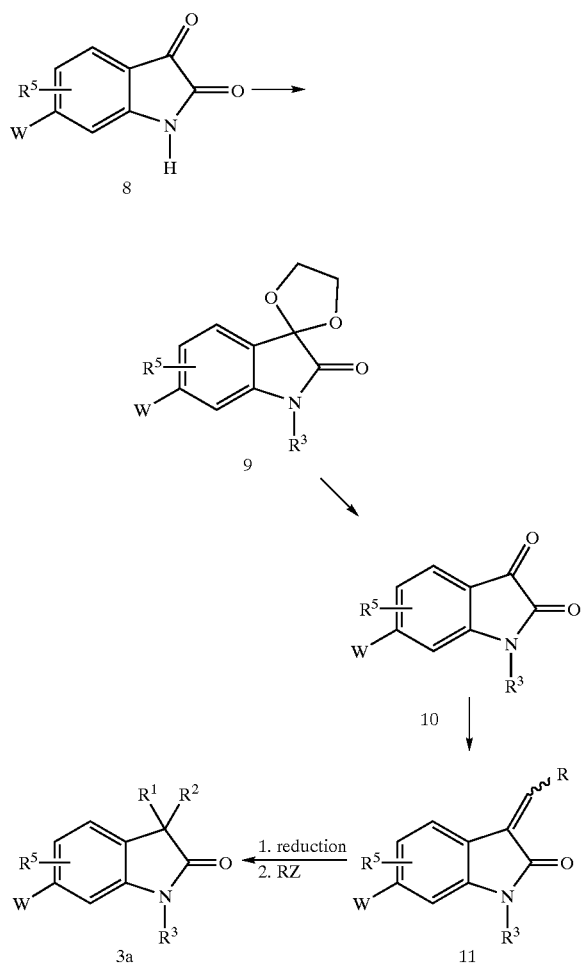

Scheme 8

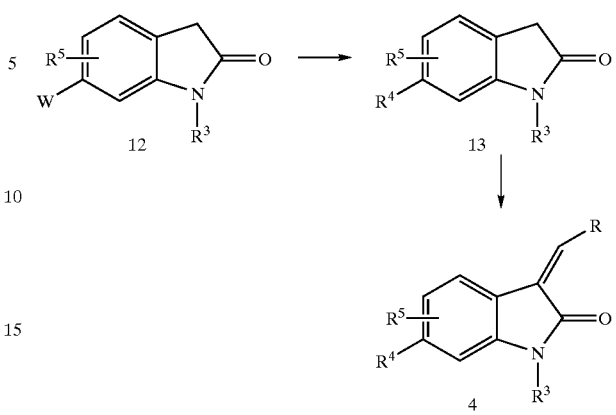

With reference to Scheme 9 below, compounds of formula 7 wherein each W is an appropriate leaving group, such as halo, and R is an appropriate carboxylic acid protecting group, such as tert-butyl, may be prepared by cyclizing a compound of formula 16 in the presence of an appropriate reagent, such as triphosgene, in an inert solvent, such as DCM, and in the presence of a base, such as diisopropylethyl amine, and optionally in the presence of a hindered base, such as DBU. The resulting compound of formula 7, wherein $R^3$ is hydrogen, may be converted to compounds of formula 7, wherein $R^3$ is other than hydrogen as defined above, using procedures familiar to those skilled in the art. Compounds of formula 16 may be prepared from compounds of formula 15 using catalytic hydrogenation conditions, such as by using platinum on carbon in a reaction-inert solvent such as ethanol in the presence of $H_2$. Compounds of formula 15 may be prepared by reacting a compound of formula 14 with a malonate derivative, such as di-tert-butyl malonate, in the presence of a base, such a sodium hydride, in an appropriate solvent, such as dimethylsulfoxide, at a temperature ranging from room temperature to 160 EC, preferably at about 100 EC.

Scheme 9

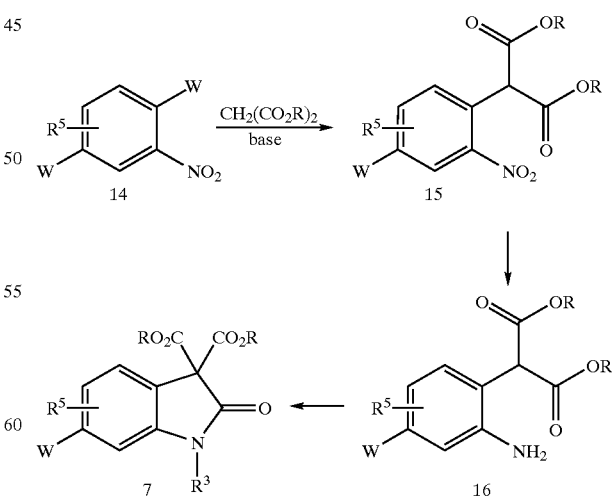

With reference to Scheme 8 below, the compounds of formula 4 which are those wherein n is 0, wherein the alkenyl-R substituent is $R^1$ or $R^2$, may be prepared by reacting a compound of formula 13 with a compound of formula RC(O)H in a suitable solvent, such as methanol, in the presence of a base such as pyrrolidine, at a temperature ranging from room temperature to reflux, preferably at about 60 EC. Compounds of formula 13 may be prepared from a compound of formula 12 using methods similar to those described in Scheme 4 above to prepare compounds of formula 2.

With reference to Scheme 10 below, an alternative method of preparing compounds of formula 5a, which are compounds of formula 5, wherein n is 0, and the $R^3$ group is bound to the oxindole nitrogen via an alkyl group, begins with a compound of formula 6 which may be reacted with a compound of formula 17, in the presence of a reducing agent, such as sodium triacetoxyborohydride, in an appropriate solvent, such as acetic acid.

Scheme 10

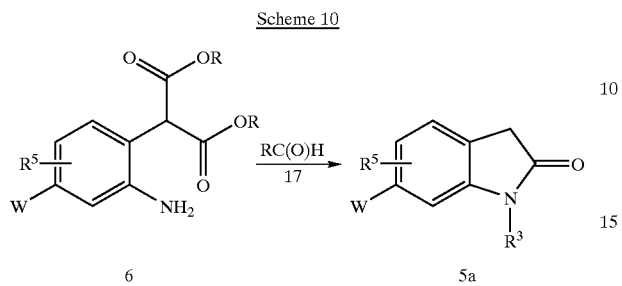

With reference to Scheme 11 below, an alternative method of preparing compounds of formula 5a, begins with a compound of formula 18 (wherein W is a leaving group, such as halo) which may be reacted in the presence of hydroxylamine, chloral hydrate, sodium sulfate, an acid, such as HCl, and in an aqueous solution to give a compound of formula 19. Compounds of formula 20 may be formed by reacting a compound of formula 19 in the presence of an acid, such as sulfuric acid (see, for example, *Synthesis*, p. 993 (1993); *J. Med. Chem.*, 29, p. 648 (1986)). Compounds of formula 20 may be converted to compounds of formula 21, wherein $R^3$ is other than hydrogen as defined above, using procedures familiar to those skilled in the art. Compounds of formula 21 may be converted to compounds of formula 5a under reductive conditions that are familiar to those skilled in the art, such as in the presence of hydrazine hydrate at an elevated temperature, preferably from about 50 to 120° C. (see, for example, *Syn. Comm.*, 24, p. 2835 (1994).

Scheme 11

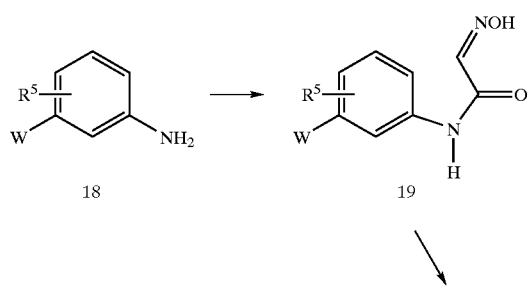

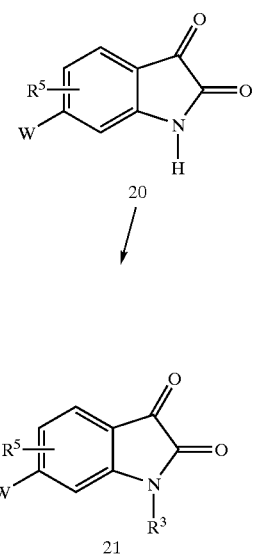

With respect to Scheme 12 below, compounds of formula 5b, which are compounds of formula 5 wherein n is 1, may be prepared starting from compounds having formula 22. Compounds having formula 23 may be prepared from compounds having formula 22 by methods familiar to those skilled in the art, such as reacting the acid compound in the presence of an appropriate reagent, such as thionyl chloride. Reaction of the compound of formula 23 in the presence of a reagent, such as lead thiocyanate leads to a compound having formula 24, which may be cyclized in the presence of a Lewis acid, such as $AlCl_3$ in an appropriate solvent, such as carbon disulfide ($CS_2$) to form a compound of formula 25. Conversion of the compound of formula 25 into the compound having formula 26 may be carried out using methods familiar to skilled practitioners, such as stirring the compound of formula 25 in a solution of aqueous base (see, *J. Org. Chem.*, 29 p. 2261 (1964)). Compounds of formula 27 may be prepared by stirring compounds of formula 26 in the presence of a dehydrating agent, such as dicyclohexylcarbodiimide (DCC), in an appropriate solvent, such as acetonitrile. Reaction of compounds of formula 27 in the presence of an amine of formula $R^3$—$NH_2$, wherein $R^3$ is as defined above, in an appropriate solvent(s) such as xylene/dioxane, at an elevated temperature, preferably from about 70 to 150° C. provides compounds of formula 5b.

Scheme 12

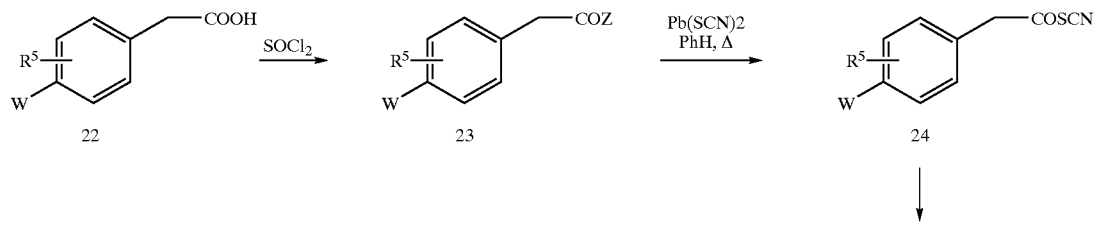

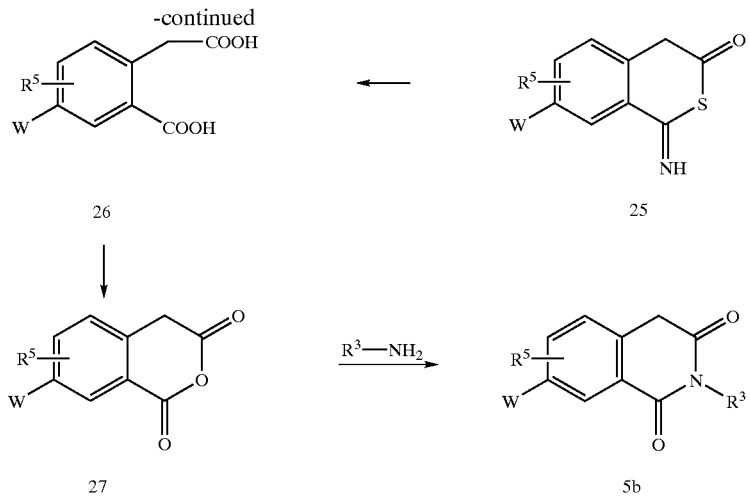

The compounds of formula 1 and some of the intermediates described above may have one or more stereogenic centers in their structure. Such stereogenic centers may be present in a R or a S configuration. Oxime moieties, such as where $R^5$ is —CH=NOR$^7$, may exist in E or Z configurations.

The compounds of formula 1 as prepared in the above processes may be racemic mixtures of enantiomers which can be separated from one another following resolution procedures familiar to those skilled in the art. The racemic compounds of formula 1 may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula 1 involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecfic methods of preparation. These methods will advantageously employ enantiomerically pure starting materials.

The compounds of formula 1 that are basic in nature are capable of forming a wide variety of different salts with various inorganic and organic acids. Although such salts must be pharmaceutically acceptable for administration to animals, it is often desirable in practice to initially isolate the compound of formula 1 from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon evaporation of the solvent, the desired solid salt is readily obtained. The desired acid addition salt can also be precipitated from a solution of the free base in an organic solvent by adding to the solution an appropriate mineral or organic acid. Cationic salts of the compounds of formula 1 are similarly prepared except through reaction of a carboxy group with an appropriate cationic salt reagent, such as sodium, potassium, calcium, magnesium, ammonium, N,N'-dibenzylethylenediamine, N-methylglucamine (meglumine), ethanolamine, tromethamine, or diethanolamine.

The compounds of formula 1 and their pharmaceutically acceptable salts, prodrugs, and solvates (hereinafter referred to, collectively, as "the therapeutic compounds") can be administered orally, transdermally (e.g., through the use of a patch), parenterally or topically. Oral administration is preferred. In general, compounds of the formula 1 and their pharmaceutically acceptable salts, prodrugs, and solvates are most desirably administered in dosages ranging from about 1.0 mg up to about 500 mg per day, preferably from about 1 to about 100 mg per day in single or divided (i.e., multiple) doses. The therapeutic compounds will ordinarily be administered in daily dosages ranging from about 0.01 to about 10 mg per kg body weight per day, in single or divided doses. Variations may occur depending on the weight and condition of the person being treated and the particular route of administration chosen. In some instances, dosage levels below the lower limit of the aforesaid range may be more than adequate, while in other cases still larger doses may be employed without causing any harmful side effect, provided that such larger doses are first divided into several small doses for administration throughout the day.

The therapeutic compounds may be administered alone or in combination with pharmaceutically acceptable carriers or diluents by either of the two routes previously indicated, and such administration may be carried out in single or multiple doses. More particularly, the novel therapeutic compounds of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Such carriers include solid diluents or fillers, sterile aqueous media and various non-toxic organic solvents, etc. Moreover, oral pharmaceutical compositions can be suitably sweetened and/or flavored.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic compound in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well-known to those skilled in the art.

Additionally, it is also possible to administer the therapeutic compounds topically and this may preferably be done by way of creams, jellies, gels, pastes, ointments and the like, in accordance with standard pharmaceutical practice.

The therapeutic compounds may also be administered to a mammal other than a human. The dosage to be administered to a mammal will depend on the animal species and the disease or disorder being treated. The therapeutic compounds may be administered to animals in the form of a capsule, bolus, tablet or liquid drench. The therapeutic compounds may also be administered to animals by injection or as an implant. Such formulations are prepared in a conventional manner in accordance with standard veterinary practice. As an alternative the therapeutic compounds may be administered with the animal feedstuff and for this purpose a concentrated feed additive or premix may be prepared for mixing with the normal animal feed.

The compounds of formula 1 exhibit activity as Ras farnesylation inhibitors and are useful in the treatment of cancer and the inhibition of abnormal cell growth in mammals, including humans. The activity of the compounds of formula 1 as Ras farnesylation inhibitors may be determined by their ability, relative to a control, to inhibit Ras farnesyl transferase in vitro. This procedure is described below.

A crude preparation of human farnesyl transferase (FTase) comprising the cytosolic fraction of homogenized brain tissue is used for screening compounds in a 96-well assay format. The cytosolic fraction is prepared by homogenizing approx. 40 grams fresh tissue in 100 ml of sucrose/MgCl$_2$/EDTA buffer (using a Dounce homogenizer; 10–15 strokes), centrifuging the homogenates at 1000 g for 10 minutes at 4° C., re-centrifuging the supernatant at 17,000 g for 15 minutes at 4° C., and then collecting the resulting supernatant. This supernatant is diluted to contain a final concentration of 50 mM Tris HCl (pH 7.5), 5 mN DTT, 0.2 M KCl, 20 mM ZnCl$_2$, 1 mM PMSF and re-centrifuged at 178,000 grams for 90 minutes at 4 G. The supernatant, termed "crude FTase" was assayed for protein concentration, aliquoted, and stored at −70° C.

The assay used to measure in vitro inhibition of human FTase is a modification of the method described by Amersham LifeScience for using their Farnesyl transferase (3H) Scintillation Proximity Assay (SPA) kit (TRKQ 7010). FTase enzyme activity is determined in a volume of 100 ml containing 50 mM N-(2-hydroxy ethyl) piperazine-N-(2-ethane sulfonic acid) (HEPES), pH 7.5, 30 mM MgCl$_2$, 20 uM KCl, 5 mM Na$_2$HPO$_4$, 5 mM dithiothreitol (DTT), 0.01% Triton X-100, 5% dimethyl sulfoxide (DMSO), 20 mg of crude FTase, 0.12 mM [3H]-farnesyl pyrophosphate ([3H]-FPP; 36000 dpm/pmole, Amersham LifeScience), and 0.2 mM of biotinylated Ras peptide KTKCVIS (Bt-KTKCVIS) that is N-terminally biotinylated at its alpha amino group and was synthesized and purified by HPLC in house. The reaction is initiated by addition of the enzyme and terminated by addition of EDTA (supplied as the STOP reagent in kit TRKQ 7010) following a 45 minute incubation at 37° C. Prenylated and unprenylated Bt-KTKCVIS is captured by adding 10 ml of steptavidin-coated SPA beads (TRKQ 7010) per well and incubating the reaction mixture for 30 minutes at room temperature. The amount of radioactivity bound to the SPA beads is determined using a MicroBeta 1450 plate counter. Under these assay conditions, the enzyme activity is linear with respect to the concentrations of the prenyl group acceptor, Bt-KTKCVIS, and crude FTase, but saturating with respect to the prenyl donor, FPP. The assay reaction time is also in the linear range.

The test compounds are routinely dissolved in 100% dimethyl sulfoxide (DMSO). Inhibition of farnesyl transferase activity is determined by calculating percent incorporation of tritiated-farnesyl in the presence of the test compound vs. its incorporation in control wells (absence of inhibitor). IC$_{50}$ values, that is, the concentration required to produce half maximal farnesylation of Bt-KTKCVIS, is determined from the dose-responses obtained.

The following Examples further illustrate the invention. In the following Examples, "Et" refers to ethyl, "Me" refers to methyl, and "Ac" refers to acetyl.

EXAMPLE 1

4-[6-(4-Cyano-phenyl)-3,3-bis-(1H-imidazol-4-ylmethyl)-2-oxo-2,3-dihydro-indol-1-ylmethyl]-N,N-dimethyl-benzenesulfonamide 1A. 2-(2-Amino-4-bromo-phenyl)-malonic acid di-tert-butyl ester 60% Sodium hydride (10.2 g, 256 mmol) in oil was washed with hexanes under an atmosphere of dry N$_2$. The solvent was subsequently decanted and the sodium hydride was suspended in 200 ml of anhydrous dimethylsulfoxide (DMSO). Di-tert-butyl malonate (57.6 ml, 256 mmol) was added dropwise to the suspension. After the addition was complete, the reaction mixture was heated to 100° C. and kept at this temperature for 1 hour. The reaction mixture was then taken out of the oil bath and 2,5-dibromonitrobenzene (32.8 g, 117 mmol) was then added portionwise over 15 minutes. The color of the reaction mixture turned purple upon addition. After the addition was complete, the reaction was reheated to 100° C. and kept at this temperature for 1 hour. The reaction mixture was then cooled to ambient temperature, poured into 200 ml of an aqueous solution of 10% ammonium chloride (NH$_4^+$Cl$^-$). The pH of this mixture was adjusted to ~7 with the addition of sodium hydrogen sulfate (NaHSO$_4$). The reaction mixture was then partitioned between 1:1 hexanes/ethyl acetate (EtOAc) and water. The water layer was washed 3 times with hexanes/EtOAc 1:1. The organic extracts were combined and washed 3 times with water, once with brine, dried over magnesium sulfate ($MgSO_4$), filtered and concentrated under vacuum to give 77.02 g of an orange oil. Some of the orange oil (65.0 g) was dissolved in 150 ml of ethanol (EtOH) in a Paar bottle. To this solution was added 10% platinum on activated carbon and the resulting mixture was hydrogenated under an atmosphere of hydrogen (45 psi) in a Paar shaker for 24 hours. The reaction mixture was then filtered through Celite. The Celite was washed with 500 ml of EtOH. The filtrates were combined and concentrated under vacuum to give a yellow oil which was subsequently stirred in 200 ml of hexanes. A white precipitate formed and was collected via suction filtration, washed with 100 ml of hexanes and dried under vacuum to give 25.2 g of the titled compound.

1B. 6-Bromo-2-oxo-1,2-dihydro-indole-3,3-dicarboxylic acid di-tert-butyl ester 2-(2-Amino-4-bromo-phenyl)-malonic acid di-tert-butyl ester (10.00 g, 25.9 mmol) and diisopropylethyl amine (22.6 ml, 129.6 mmol) were dissolved in 100 ml of anhydrous dichloromethane (DCM) under an atmosphere of dry $N_2$. The solution was cooled to 0° C. and triphosgene (2.82 g, 9.50 mmol) was added portionwise over a period of 15 minutes. After the addition was complete, the reaction mixture was warmed to ambient temperature and stirred for 1.5 hours after which time 1,8-diazabicyclo[5.4.0]undec-7-ene (19.4 ml, 129.5 mmol) was added and the mixture was stirred for an additional 1 hour. The reaction mixture was then partitioned between water and DCM. The DCM layer was then washed 3 times with 10% aqueous $NaHSO_4$, dried over $MgSO_4$, filtered and concentrated under vacuum to give a green foam. The green foam was stirred in hexanes overnight. The precipitate was collected and washed with hexanes, dried under vacuum to give 5.10 g of the titled compound as a white solid.

1C. 6-Bromo-1-(4-dimethylsulfamoyl-benzyl)-2-oxo-1,2-dihydro-indole-3,3-dicarboxylic acid di-tert-butyl ester 6-Bromo-2-oxo-1,2-dihydro-indole-3,3-dicarboxylic acid di-tert-butyl ester (5.10 g, 12.4 mmol) was dissolved in 40 ml of anhydrous N,N-dimethylformamide (DMF) under an atmosphere of dry $N_2$. The solution was cooled to 0° C. after which time 60% sodium hydride in oil (500 mg, 12.4 mmol) was added and the solution was then stirred for 15 minutes at this temperature. The reaction mixture was the warmed to ambient temperature and stirred for 15 minutes after which time 4-bromomethyl-N,N-dimethyl-benzenesulfonamide (3.44 g, 12.4 mmol) was added. The mixture was stirred overnight after which time it was concentrated under vacuum and partitioned between DCM and water. The DCM layer was washed 3 more times with water, once with brine, dried over $MgSO_4$, filtered and concentrated under vacuum to give 8.63 g of the titled compound as a yellow solid 1D. 4-(6-Bromo-2-oxo-2,3-dihydro-indol-1-ylmethyl)-N,N-dimethyl-benzenesulfonamide 6-Bromo-1-(4-dimethylsulfamoyl-benzyl)-2-oxo-1,2-dihydro-indole-3,3-dicarboxylic acid di-tert-butyl ester (10.0 g, 16.4 mmol) was dissolved in 50 ml of trifluoroacetic acid (TFA) under an atmosphere of dry $N_2$ and stirred overnight at ambient temperature. The reaction mixture was then concentrated under vacuum and partitioned between DCM and saturated aqueous sodium bicarbonate ($NaHCO_3$). The DCM layer was then dried over $MgSO_4$, filtered and concentrated under vacuum to give 6.05 g of the titled compound as a white solid.

1E. 4-[6-(4-Cyano-phenyl)-2-oxo-2,3-dihydro-indol-1-ylmethyl]-N,N-dimethyl-benzenesulfonamide 4-(6-Bromo-2-oxo-2,3-dihydro-indol-1-ylmethyl)-N,N-dimethyl-benzenesulfonamide (1.60 g, 4.24 mmol) and tetrakis(triphenylphosphine)palladium (0) (195 mg, 0.17 mmol) were dissolved in a solution of 25 ml of toluene and 4 ml of EtOH under an atmosphere of dry $N_2$. To the reaction mixture was added a solution of aqueous sodium carbonate ($Na_2CO_3$) (1.03 g, 9.75 mmol) dissolved in 6 ml of water followed by 4-cyanobenzene boronic acid (1.55 g, 10.6 mmol). The reaction mixture was heated to 100° C. and stirred at this temperature overnight. The reaction mixture was concentrated under vacuum and then partitioned between DCM and saturated aqueous $NaHCO_3$. The DCM layer was dried over $MgSO_4$, filtered and concentrated under vacuum to give a brown oil. The brown oil was chromatographed on silica gel eluting with a gradient from DCM to DCM/MeOH (98:2) to give 1.15 g of the titled compound as an orange solid in 63% yield.

1F. 4-[6-(4-Cyano-phenyl)-2-oxo-3,3-bis-(1-trityl-1H-imidazol4-ylmethyl)-2,3-dihydro-indol-1-ylmethyl]-N,N-dimethyl-benzenesulfonamide 4-[6-(4-Cyano-phenyl)-2-oxo-2,3-dihydro-indol-1-ylmethyl]-N,N-dimethyl-benzenesulfonamide (216 mg, 0.501 mmol) and 4-chloromethyl-1-trityl-1H-imidazole compound (402 mg, 1.12 mmol) were dissolved in 5 ml of anhydrous THF under an atmosphere of dry $N_2$. To this solution was added 95% potassium hexamethyldisilylamide (KHMDS) (230 mg, 1.10 mmol) and the reaction mixture was subsequently stirred overnight. The reaction mixture was partitioned between DCM and saturated aqueous $NaHCO_3$. The DCM layer was dried over sodium sulfate ($Na_2SO_4$), filtered and concentrated under vacuum to give a purple foam which was chromatographed on flash silica gel eluting with a gradient of chloroform ($CHCl_3$) to $CHCl_3$/MeOH/$NH_4OH$ (98/2/0.01) to give 300 mg of the titled compound as a pink oil.

1G. 4-[6-(4-Cyano-phenyl)-3,3-bis-(1H-imidazol-4-ylmethyl)-2-oxo-2,3-dihydro-indol-1-ylmethyl]-N,N-dimethyl-benzenesulfonamide 4-[6-(4-Cyano-phenyl)-2-oxo-3,3-bis-(1-trityl-1H-imidazol-4-ylmethyl)-2,3-dihydro-indol-1-ylmethyl]-N,N-dimethyl-benzenesulfonamide (0.3 g, 0.4 mmol) was dissolved in a solution of 4.0 ml of TFA and 500 μL of triethylsilane under an atmosphere of dry $N_2$ and stirred for 1 hour. The heterogeneous mixture was concentrated under vacuum and partitioned between aqueous 0.1 N HCl and ethyl ether ($Et_2O$). The water layer was washed with $Et_2O$ and then basified to pH~9 with sodium hydroxide (NaOH). The water layer was then washed 3 times with DCM. The DCM layers were combined and dried over $Na_2SO_4$, filtered and concentrated under vacuum to give 13 mg of the titled compound as a purple solid.

C.I. m/z 592 [M+1]; $^1$H NMR ($CDCl_3$) □7.68 (d, J=8.3 Hz, 2H), 7.49 (d, J=8.3 Hz, 2H), 7.45 (d, J=8.5 Hz, 2H), 6.90–7.43 (m, 6H), 6.46 (d, J=1.4 Hz, 1H), 6.28 (d, J=1.0 Hz, 2H), 4.72 (s, J=2H), 3.29 (d, J=14.1 Hz, 2H), 3.21 (d, J=14.1 Hz, 2H), 2,54 (s, 6H).

EXAMPLE 2

4-[3,3-Bis-(3H-imidazol-4-ylmethyl)-1-naphthalen-1-ylmethyl-2-oxo-2,3-dihydro-1H-indol-6-yl]-benzonitrile 2A. 6-Bromo-1-naphthalen-1-ylmethyl-1,3-dihydro-indol-2-one 2-(2-Amino-4-bromo-phenyl)-malonic acid di-tert-butyl ester (7.73 g, 20.0 mmol) and 1-napthylaldehyde (3.0 ml, 22.0 mmol) were dissolved in 80 ml of acetic acid (AcOH) under an atmosphere of dry $N_2$. To this solution was added 95% sodium triacetoxyborohydride (NaHB(OAc)$_3$) (5.8 g, 26 mmol) and the solution was stirred for 45 minutes. The reaction mixture was concentrated under vacuum and then stirred in 100 ml of a 1:1 solution of DCM/water. To this mixture was slowly added NaHCO$_3$ until the pH~8. The DCM layer was then washed with saturated aqueous NaHCO$_3$ and dried over MgSO$_4$, filtered and concentrated under vacuum to give a foam which was subsequently dissolved in a solution of 80 ml of TFA and 10 ml of triethylsilane under an atmosphere of dry N$_2$. The mixture was stirred overnight after which time the precipitate was collected, washed with hexanes and dried under vacuum to give 6.43 g of the titled compound as a white solid in 90% yield.

2B. 4-[3,3-Bis-(3H-imidazol-4-ylmethyl)-1-naphthalen-1-ylmethyl-2-oxo-2,3-dihydro-1H-indol-6-yl]-benzonitrile 4-[3,3-Bis-(3H-imidazol-4-ylmethyl)-1-naphthalen-1-ylmethyl-2-oxo-2,3-dihydro-1H-indol-6-yl]-benzonitrile was prepared by using the methods outlined in steps 1E-G in example 1 except that 6-bromo-1-naphthalen-1-ylmethyl-1,3-dihydro-indol-2-one was substituted for 4-(6-bromo-2-oxo-2,3-dihydro-indol-1-ylmethyl)-N,N-dimethyl-benzenesulfonamide in step 1E.

$^1$H NMR (CD$_3$OD) □8.18 (m, 1H), 7.45–7.90 (m, 12H), 7.28 (m, 1H), 7.05 (s, 1H), 6.82 (d, J=0.9 Hz, 1H), 6.56 (d, J=8.2 Hz, 1H), 5.32 (s, 2H), 3.59 (d, J=14 Hz, 2H), 3.39 (d, J=14 Hz, 2H).

EXAMPLE 3

4-[1-Adamantan-1-ylmethyl-3-(1H-imidazol-4-ylmethyl)-3-(3H-imidazol4-ylmethyl)-2-oxo-2,3-dihydro-1H-indol-6-yl]-benzonitrile 3A. 1-Adamantan-1-ylmethyl-6-bromo-1,3-dihydro-indol-2-one 1-Adamantan-1-ylmethyl-6-bromo-1,3-dihydro-indol-2-one was prepared by using the methods outlined in step 2A of example 2 except that adamantane-1-carbaldehyde was substituted for naphthalene-1-carbaldehyde.

3B. 4-(1-Adamantan-1-ylmethyl-2-oxo-2,3-dihydro-1H-indol-6-yl)-benzonitrile

1-Adamantan-1-ylmethyl-6-bromo-1,3-dihydro-indol-2-one (1.06 g, 2.9 mmol) was dissolved in a previously degassed solution of 18 ml of toluene and 3 ml of EtOH under an atmosphere of dry N$_2$. To this solution was added tetrakis(triphenylphosphine)palladium (0) (133 mg, 0.12 mmol) followed by a solution of Na$_2$CO$_3$ (707 mg, 6.67 mmol) dissolved in 5 ml of water. To this solution was added 4-cyanobenzene boronic acid (640 mg, 4.35 mmol) and the reaction mixture was then heated to 100° C. and reacted at this temperature for 4 hours. The reaction mixture was then cooled to ambient temperature and partitioned between DCM and saturated aqueous NaHCO$_3$. The aqueous layer was extracted two more times with DCM and the DCM extracts were then combined and washed with brine. The organic layer was then dried over Na$_2$SO$_4$, filtered and concentrated under vacuum to give a brown oil which was then triturated with Et$_2$O to give 400 mg of the titled compound as a tan oil.

3C. 4-[1-Adamantan-1-ylmethyl-2-oxo-3,3-bis-(1-trityl-1H-imidazol-4-ylmethyl)-2,3-dihydro-1H-indol-6-yl]-benzonitrile 4-(1-Adamantan-1-ylmethyl-2-oxo-2,3-dihydro-1H-indol-6-yl)-benzonitrile (191 mg, 0.50 mmol) and 4-chloromethyl-1-trityl-1H-imidazole compound (449 mg, 1.25 mmol) were dissolved in 5 ml of anhydrous THF under an atmosphere of dry N$_2$. To this solution was added 95% KHMDS (220 mg, 1.05 mmol) and the reaction mixture was subsequently stirred overnight. The reaction mixture was partitioned between DCM and saturated aqueous NaHCO$_3$. The DCM layer was dried over Na$_2$SO$_4$, filtered and concentrated under vacuum to give a purple foam which was chromatographed on flash silica gel eluting with a gradient of CHCl$_3$ to CHCl$_3$/MeOH/NH$_4$OH (98/2/0.01) to give 136 mg of the titled compound as a pink oil.

3D. 4-[1-Adamantan-1-ylmethyl-3-(1H-imidazol-4-ylmethyl)-3-(3H-imidazol-4-ylmethyl)-2-oxo-2,3-dihydro-1H-indol-6-yl]-benzonitrile 4-[1-Adamantan-1-ylmethyl-2-oxo-3,3-bis-(1-trityl-1H-imidazol-4-ylmethyl)-2,3-dihydro-1H-indol-6-yl]-benzonitrile (136 mg, 0.132 mmol), was dissolved in a 1:1 solution of formic acid and water. The reaction mixture was heated to 45° C. and stirred at this temperature for 1 hour. The reaction mixture was cooled to ambient temperature, filtered and the filtrate was concentrated under vacuum to remove the formic acid. The resulting solution was lyopholised to give 28 mg of the bis-formate salt of the titled compound as a fluffy white solid.

C.I. m/z 543 [M+1]; $^1$H NMR (CDCl$_3$) □7.96 (brs, 2H), 7.79 (m, 4H), 7.45 (s, 2H), 7.22 (m, 2H), 7.14 (s, 1H), 6.53 (brs, 2H), 3.25–3.37 (m, 6H), 1.86 (brs, 3H), 1.65 (m, 3H), 1.54 (m, 3H), 1.35 (brs, 6H).

EXAMPLE 4

4-[3-(1H-Imidazol-4-ylmethyl)-3-(3H-imidazol-4-ylmethyl)-2-oxo-1-quinolin-4-ylmethyl-2,3-dihydro-1H-indol-6-yl]-benzonitrile 4A. 6-Bromo-1-quinolin-4-ylmethyl-1,3-dihydro-indol-2-one 2-(2-Amino-4-bromo-phenyl)-malonic acid di-tert-butyl ester (1.93 g, 5.0 mmol) and 4-quinolinecarboxaldehyde (890 mg, 5.50 mmol) were dissolved in 20 ml of AcOH under an atmosphere of dry N$_2$. To this solution was added 95% NaHB(OAc)$_3$ (1.45 g, 6.5 mmol) and the solution was stirred for 30 minutes. The reaction mixture was concentrated under vacuum and then stirred in 60 ml of a 1:1 solution of DCM/water. To this mixture was slowly added NaHCO$_3$ until the pH~8. The DCM layer was then washed with saturated aqueous NaHCO$_3$ and dried over Na$_2$SO$_4$, filtered and concentrated under vacuum to give a golden oil which was subsequently dissolved in a solution of 20 ml of TFA and 2.5 ml of triethylsilane under an atmosphere of dry N$_2$. The mixture was stirred overnight after which time the reaction mixture was concentrated under vacuum and then partitioned between DCM and saturated aqueous NaHCO$_3$. The DCM layer was dried over Na$_2$SO$_4$, filtered and concentrated under vacuum to give a brown solid which, after trituration with Et$_2$O, gives the tilted compound as a white solid.

4B. 4-[3-(1H-Imidazol-4-ylmethyl)-3-(3H-imidazol-4-ylmethyl)-2-oxo-1-quinolin-4-ylmethyl-2,3-dihydro-1H-indol-6-yl]-benzonitrile 4-[3-(1H-Imidazol-4-ylmethyl)-3-(3H-imidazol-4-ylmethyl)-2-oxo-1-quinolin-4-ylmethyl-2,3-dihydro-1H-indol-6-yl]-benzonitrile was prepared by using the methods outlined in example 3 except that 6-bromo-1-quinolin-4-ylmethyl-1,3-dihydro-indol-2-one was substituted for 1-adamantan-1-ylmethyl-6-bromo-1,3-dihydro-indol-2-one to in step 3B to give the bisformate salt of the titled compound.

C.I. m/z 536 [M+1] $^1$H NMR (CD$_3$OD) □8.53 (m, 1H), 8.19 (d, J=8.5 Hz, 1H), 8.02 (d, J=8.3 Hz, 1H), 7.96 (brs, 2H), 7.80 (m, 1H), 7.56–7.70 (m, 8H), 7.49 (m, 1H), 6.86 (s, 1H), 6.66 (brs, 2H), 6.00 (m, 1H), 5.40 (s, 2H), 3.42 (m, 4H).

EXAMPLE 5

4-[6-(4-Formyl-phenyl)-2-oxo-3,3-bis-pyridin-4-ylmethyl-2,3-dihydro-indol-1-ylmethyl]-N,N-dimethyl-benzenesulfonamide 5A. 6'-Bromospiro<1,3-dioxolane-2,3'-indolin>-2'-one 6-Bromo-1H-indole-2,3-dione (2.00 g, 8.85 mmol) was suspended in a solution of 150 ml of benzene and 5 ml of ethylene glycol under atmosphere of dry N$_2$. To this heterogeneous solution was added p-toluenesulphonic acid (100 mg, 0.53 mmol) and the mixture was heated to reflux. A Dean Stark trap was used to remove the water that was generated during the reaction. After ~3 hours, the mixture became homogeneous and was subsequently cooled to ambient temperature and then partitioned between saturated aqueous NaHCO$_3$ and EtOAc. The organic layer was then washed with water and then brine, dried over MgSO$_4$, filtered and concentrated under vacuum to give 2.34 g of the titled compound as a yellow solid.

5B. 6'-Bromo-(1'-4-N,N-dimethyl-bezenesulfonamide) spiro<1,3-dioxolane-2,3'-indolin>-2'-one 6'-Bromospiro<1,3-dioxolane-2,3'-indolin>-2'-one (771 mg, 2.85 mmol) was dissolved in 13 ml of anhydrous DMF under an atmosphere of dry N$_2$. To this solution was added 126 mg (3.14 mmol) of NaH (60% in oil). After H$_2$ evolution ceased (~10 minutes), 4-bromomethyl-N,N-dimethyl-benzenesulfonamide (794 mg, 2.85 mmol) was added to the reaction mixture. The reaction was stirred overnight at ambient temperature and then partitioned between DCM and water. The DCM layer was washed 4 more times with water, dried over Na$_2$SO$_4$, filtered and concentrated under vacuum to give 1.29 g of a yellow solid as the titled compound.

5C. 4-(6-Bromo-2,3-dioxo-2,3-dihydro-indol-1-ylmethyl)-N,N-dimethyl-benzenesulfonamide 6'-Bromo-(1'-4-N,N-dimethyl-bezenesulfonamide) spiro<1,3-dioxolane-2,3'-indolin>-2'-one (2.45 g, 5.24 mmol) was dissolved in 5 ml of sulfuric acid and stirred for 20 minutes at ambient temperature. To the reaction mixture was added ice followed by 50 ml of water. The reaction mixture was partitioned between DCM and water. The DCM layer was successively washed with water and brine, dried over MgSO$_4$, filtered and concentrated under vacuum to give 2.20 g of an orange solid as the titled compound.

5D. 4-(6-Bromo-2-oxo-3-pryridin-4-ylmethylene-2,3-dihydro-indol-1-ylmethyl)-N,N-dimethyl-benzenesulfonamide 4-(6-Bromo-2,3-dioxo-2,3-dihydro-indol-1-ylmethyl)-N,N-dimethyl-benzenesulfonamide (2.20 g, 5.24 mmol) was dissolved in a solution of AcOH (50 ml) and acetic anhydride (50 ml) under an atmosphere of dry N$_2$. To this mixture was added 4-picoline (1.0 ml, 10.5 mmol) and then reaction mixture was subsequently heated to reflux and reacted at this temperature overnight. The reaction mixture was cooled to ambient temperature and concentrated under vacuum to give a dark oil. The oil was partitioned between DCM and saturated aqueous NaHCO$_3$. The DCM layer was then dried over Na$_2$SO$_4$, filtered and concentrated under vacuum to give a dark oil and was chromatographed on silica gel eluting with a gradient from EtOAc/hexanes (30:70) to EtOAc/hexanes (70:30) to give 1.45 g of the titled compound as an orange solid.

5E. 4-(6-Bromo-2-oxo-3,3-bis-pyridin-4-ylmethyl-2,3-dihydro-indol-1-ylmethyl)-N,N-dimethyl-benzenesulfonamide 4-(6-Bromo-2-oxo-3-pyridin-4-ylmethylene-2,3-dihydro-indol-1-ylmethyl)-N,N-dimethyl-benzenesulfonamide (1.45 g, 2.92 mmol) was dissolved in a previously degassed solution of 50 ml of methanol and 50 ml of THF under an atmosphere of dry N$_2$. To this solution was added sodium borohydride (177 mg, 4.67 mmol). The reaction was stirred at ambient temperature for 1.5 hours after which time 11.7 ml of aqueous 1.0 N potassium hydroxide (KOH) was added followed by the addition of 4-picolyl chloride hydrochloride (520 mg, 3.08 mmol). The reaction mixture was then stirred at ambient temperature for 2 hours after which time the reaction mixture was concentrated under vacuum to give a dark oil. The dark oil was partitioned between DCM and saturated aqueous NaHCO$_3$. The DCM layer was then washed with brine, dried over Na$_2$SO$_4$, filtered and concentrated under vacuum to give a dark oil which was chromatographed on flash silica gel eluting with a gradient from EtOAc/hexanes (60:40) to EtOAc/Hexanes (80:20) to give 650 mg of the titled compound as a pink solid.

5F. 4-[6-(4-Formyl-phenyl)-2-oxo-3,3-bis-pyridin-4-ylmethyl-2,3-dihydro-indol-1-ylmethyl]-N,N-dimethyl-benzenesulfonamide 4-(6-Bromo-2-oxo-3,3-bis-pyridin-4-ylmethyl-2,3-dihydro-indol-1-ylmethyl)-N,N-dimethyl-benzenesulfonamide (306 mg, 0.517 mmol) was dissolved in a solution of 6 ml of toluene and 1 ml of EtOH under an atmosphere of dry N$_2$. To this solution was added tetrakis (triphenylphosphine)palladium (0) (34 mg, 0.029 mmol) followed by a solution of Na$_2$CO$_3$ (126 mg, 1.19 mmol) dissolved in 1 ml of water and 4-formylbezeneboronic acid (116 mg, 0.776 mmol). The reaction mixture was heated to 100° C. and reacted at this temperature overnight. The reaction mixture was cooled to ambient temperature and then partitioned between EtOAc and saturated aqueous NaHCO$_3$. The aqueous layer was washed two more times with EtOAc. The combined EtOAc layers were dried over Na$_2$SO$_4$, filtered and concentrated under vacuum to give a dark oil. The oil was purified using radial chromatography eluting with MeOH/DCM (5:95) to give 258 mg of the titled compound as a solid.

C.I. m/z 617 [M+1]; $^1$H NMR (CDCl$_3$) □10.00 (s, 1H), 8.30 (m, 4H), 7.86 (d, J=8.4 Hz, 2H), 7.51 (m, 5H), 7.41 (dd, J=1.5, 7.7 Hz, 1H), 6.85 (m, 4H), 6.49 (d, J=8.0 Hz, 2H), 6.36 (s, 1H), 4.60 (s, 2H), 3.43 (d, J=12.8 Hz, 2H), 3.27 (d, J=12.8 Hz, 2H), 2.66 (s, 6H).

EXAMPLE 6

4-[6-(4-Cyano-phenyl)-2-oxo-3,3-bis-pyridin-4-ylmethyl-2,3-dihydro-indol-1-ylmethyl]-N,N-dimethyl-benzenesulfonamide 4-[6-(4-Formyl-phenyl)-2-oxo-3,3-bis-pyridin-4-ylmethyl-2,3-dihydro-indol-1-ylmethyl]-N,N-dimethyl-benzenesulfonamide (248 mg, 0.402 mmol) was dissolved in a solution of 5 ml of DCM and 2 ml of EtOH under an atmosphere of dry N$_2$. To this solution was added hydroxylamine hydrochloride (34.7 mg, 0.50 mmol) and the mixture was stirred overnight at ambient temperature. The reaction mixture was then concentrated under vacuum and the residue was partitioned between DCM and saturated aqueous NaHCO$_3$. The DCM layer was dried over Na$_2$SO$_4$, filtered and concentrated under vacuum to give 170 mg of {6-[4-(hydroxyimino-methyl)-phenyl]-2-oxo-3,3-bis-pyridin-4- ylmethyl-2,3-dihydro-indol-1-ylmethyl}-N,N-dimethyl-benzenesulfonamide as a tan solid. This compound was dissolved in 3 ml of anhydrous DCM under an atmosphere of dry $N_2$. To this solution was added triethylamine (120 □L, 0.86 mmol) followed by the addition of p-toluenesulphonyl chloride (57 mg, 0.30 mmol). The reaction mixture was stirred at ambient temperature for 40 minutes after which time it was partitioned between DCM and saturated aqueous $NaHCO_3$, dried over $Na_2SO_4$, filtered and concentrated under vacuum to give an orange film. The foam was purified via radial chromatography eluting with MeOH/DCM (5:95) to give 82 mg of the titled compound as a tan solid.

C.l. m/z 614 [M+1]; $^1$H NMR (CDCl$_3$) □8.26 (m, 4H), 7.62 (d, J=8.1 Hz, 2H), 7.50 (m, 3H), 7.41 (d, J=8.3 Hz, 2H), 7.35 (dd, J=1.2, 7.7 Hz, 1H), 6.82 (m, 4H), 6.46 (d, J=8.1 Hz, 2H), 6.29 (s, 1H), 4.58 (s, 2H), 3.41 (d, J=12.7 Hz, 2H), 3.26 (d, J=12.7 Hz, 2H), 2.65 (s, 6H).

EXAMPLE 7

4-(1-Naphthalen-1-ylmethyl-2-oxo-3,3-bis-pyridin-4-ylmethyl-2,3-dihydro-1H-indol-6-yl)-benzonitrile 7A. 6-Bromo-1-naphthalen-1-ylmethyl-3,3-bis-pyridin-4-ylmethyl-1,3-dihydro-indol-2-one 6-Bromo-1-naphthalen-1-ylmethyl-1,3-dihydro-indol-2-one (195 mg, 0.554 mmol) was dissolved in 1 ml of THF and was then added to a previously degassed solution of 3 ml of THF and 5 ml of aqueous 1 N KOH under an atmosphere of dry $N_2$. To this solution was added 4-picolyl chloride hydrochloride (275 mg, 1.67 mmol). The reaction mixture was then stirred at ambient temperature for 2 hours after which time the reaction mixture was concentrated under vacuum to give a green oil. The oil was partitioned between DCM and saturated aqueous $NaHCO_3$. The DCM layer was then washed with brine, dried over $Na_2SO_4$, filtered and concentrated under vacuum to give a dark oil which was chromatographed on flash silica gel eluting with a gradient from EtOAc/hexanes (50:50) to EtOAc to EtOAc/MeOH (95:5) to give 140 mg of the titled compound as a colorless oil.

7B. 4-[6-(4-Formyl-phenyl)-2-oxo-3,3-bis-pyridin-4-ylmethyl-2,3-dihydro-indol-1-ylmethyl]-N,N-dimethyl-benzenesulfonamide The title compound was prepared by following the procedure outlined in step 5E of example 5 with the proviso that 6-bromo-1-naphthalen-1-ylmethyl-3,3-bis-pyridin-4-ylmethyl-1,3-dihydro-indol-2-one was used in the place of 4-(6-bromo-2-oxo-3,3-bis-pyridin-4-ylmethyl-2,3-dihydro-indol-1-ylmethyl)-N,N-dimethyl-benzenesulfonamide.

7C. 4-(1-Naphthalen-1-ylmethyl-2-oxo-3,3-bis-pyridin-4-ylmethyl-2,3-dihydro-1H-indol-4-yl)-benzonitrile The title compound was prepared by following the procedure used in example 6 with the provisio that 4-[6-(4-formyl-phenyl)-2-oxo-3,3-bis-pyridin-4-ylmethyl-2,3-dihydro-indol-1-ylmethyl]-N,N-dimethyl-benzenesulfonamide was used in the place of 4-[6-(4-formyl-phenyl)-2-oxo-3,3-bis-pyridin-4-ylmethyl-2,3-dihydro-indol-1-ylmethyl]-N,N-dimethyl-benzenesulfonamide.

C.l. m/z 557 [M+1]; $^1$H NMR (CDCl$_3$) □8.31 (m, 4H), 7.86 (d, J=8.1 Hz, 1H), 7.81 (dd, J=1.7, 7.3 Hz, 1H), 7.32–7.66 (m, 9H), 6.98 (t, J=7.6 Hz, 1H), 6.86 (m, 4H), 6.34 (d, J=1.5 Hz, 1H), 5.45 (d, J=7.3 Hz, 1H), 5.00 (s, 2H), 3.45 (d, J=12.7 Hz, 2H), 3.27 (d, J=12.7 Hz, 2H).

EXAMPLE 8

4-(2-Oxo-3,3-bis-pyridin-4-ylmethyl-1-quinolin-4-ylmethyl-2,3-dihydro-1H-indol-6-yl)-benzonitrile The title compound was prepared by following the procedures in example 7 with the provisio that 6-bromo-1-quinolin-4-ylmethyl-1,3-dihydro-indol-2-one was used in the place of 6-bromo-1-naphthalen-1-ylmethyl-1,3-dihydro-indol-2-one in step 7A.

C.l. m/z 558 [M+1]; $^1$H NMR (CDCl$_3$) □8.26 (d, J=4.4 Hz, 1H), 8.22 (m, 4H), 8.08 (d, J=8.3 Hz, 1H), 7.96 (d, J=8.5 Hz, 1H), 7.90 (d, J=8.9 Hz, 1H), 7.72 (m, 1H), 7.48–62 (m, 7H), 7.00 (m, 4H), 6.66 (m, 1H), 5.28 (d, J=4.4 Hz, 1H), 5.20 (s, 2H), 3.52 (d, J=12.7 Hz, 2H), 3.46 (d, J=12.7 Hz, 2H).

EXAMPLE 9

4-[1-Adamantan-1-ylmethyl-3,3-bis-(3-methyl-3H-imidazol-4-ylmethyl)-2-oxo-2,3-dihydro-1H-indol-6-yl]-benzonitrile 9A. 2-{2-[(Adamantan-1-ylmethyl)-amino]4-bromo-phenyl}-malonic acid di-tert-butyl ester To a solution of adamantane-1-carbaldehyde (3.77 g, 23 mmol) in acetic acid (45 ml) was added 2-(2-amino-4-bromo-phenyl)-malonic acid di-tert-butyl ester (4.44 g, 11.5 mmol) followed by addition of sodium triacetoxyborohydride (3.41 g, 16 mmol). The reaction mixture stirred for 30 minutes. After removal of the acetic acid, the reaction mixture was then partitioned between water and chloroform. Powdered $K_2CO_3$ was added and the pH of the aqueous layer was adjusted to 8. After separation, the organic layer was then washed with brine, dried over $MgSO_4$, filtered and concentrated under vacuum to give the crude title compound of 9A as a brown oil (7.81 9), which was used in the next step without further purification.

9B. 1-Adamantan-1-ylmethyl-6-bromo-1,3-dihydro-indol-2-one

To a solution of the title compound of 1A (crude, 7.81 g) in THF (35 ml) was added triethylsilane (5.51 ml, 34.47 mmol). The reaction mixture was stirred at ambient temperature for 15 hours after which time the reaction .mixture was filtered to obtain a white solid. The white solid was washed with hexane and was then partitioned between 10% aqueous $K_2CO_3$ and chloroform. After separation, the organic layer was washed with brine, dried over $MgSO_4$, filtered and concentrated under vacuum to give the title compound of the title compound of 9B as a white solid (4.03 g, 97% yield for two steps).

9C. 4-(1-Adamantan-1-ylmethyl-2-oxo-2,3-dihydro-1H-indol-6-yl)-benzonitrile

To a solution of 1-adamantan-1-ylmethyl-6-bromo-1,3-dihydro-indol-2-one (1.85 g, 5.13 mmol) in toluene (23 ml) and ethanol (21 ml) were added tetrakis(triphenylphosphine) palladium (0.60 g, 0.513 mmol), sodium carbonate (1.09 g, 10.27 mmol) in water (11 ml) and solid 4-cyanophenylboronic acid (1.51 g, 10.27 mmol). The mixture was heated at 100° C. overnight. The reaction mixture was partitioned between chloroform and aqueous saturated potassium carbonate (50 ml). The organic layer was washed with brine, dried over $MgSO_4$, filtered and concentrated under vacuum to give the crude product. This was chromatographed on flash silica gel eluting with a 15% ethyl acetate in hexane to give the title compound of 9C as a white solid (0.594 g, 30.3% yield).

9D. 4-[1-Adamantan-1-ylmethyl-3,3-bis-(3-methyl-3H-imidazol-4-ylmethyl)-2-oxo-2,3-dihydro-1H-indol-6-yl]-benzonitrile 4-(1-adamantan-1-ylmethyl-2-oxo-2,3-dihydro-1H-indol-6-yl)-benzonitrile (445 mg, 1.165 mmol) and 5-chloromethyl-1-methyl-imidazole hydrochloride (580 mg, 3.49 mmol) were dissolved in 12 ml of THF under an atmosphere of dry $N_2$. To this solution was added a solution of 40% aqueous sodium hydroxide (6.6 ml) dropwise at room temperature. The reaction mixture was stirred at room temperature overnight. The reaction mixture was partitioned between chloroform and aqueous saturated $K_2CO_3$. The organic layer was dried over $MgSO_4$, filtered and concentrated under vacuum to give the crude product which was chromatographed on flash silica gel eluting with a gradient of $CHCl_3/MeOH/NH_4OH$ (99/1/0.1) to (95/5/0.5), providing the title compound of Example 9 as a white solid (294 mg, 0.515 mmol, 44.2% yield).

C.l. m/z 571.2 [M+1].

EXAMPLE 10

4-(7-Methyl-1-naphthalen-2-ylmethyl-2-oxo-3,3-bis-pyridin-4-ylmethyl-2,3-dihydro-1H-indol-6-yl)-benzonitrile 10A. 6-Bromo-7-methyl-1H-indole-2,3-dione To a solution of 3-bromo-2-methyl-phenylamine (10.47 g, 56.29 mmol) in water (100 ml) was added 5% HCl (80 ml), hydroxylamine HCl (12.90 g, 185.7 mmol) and sodium sulfate (53.9 g, 371.5 mmol). The mixture was brought to a boil, and immediately a boiling solution of chloral hydrate (11.63 g, 70.36 mmol) in water (100 ml) was added and the combined mixture kept boiling for 1 h. It was cooled, and diluted ammonia hydroxide (30 ml of concentrated $NH_4OH$ in 300 ml of $H_2O$) was added. The product precipitated out and was filtered and re-dissolved in ethyl acetate. The filtrate was extracted with ethyl acetate. The ethyl acetate solutions were combined, dried and evaporated to dryness to afford 13.73 g of a brown solid. This solid was added at 0° C. to a rapidly stirred solution of concentrated $H_2SO_4$ (100 ml) and water (15 ml). After stirring for 1 hour at 0° C., the reaction mixture was warmed up to 75° C. for 0.5 h. After cooling to room temperature, the solution was poured onto a cracked ice with $NH_4OH$ (250 ml). The crude product was precipitated out as an orange solid. It was collected and washed with methanol to give 5.27 g of an orange solid. The methanol filtrate was treated with water to form a precipitate. Filtration afforded an additional 3.34 g of the product, with a total of 9.11 g of the title compound of 2A (75% yield).

10B. 6-Bromo-7-methyl-1-naphthalen-2-ylmethyl-1H-indole-2,3-dione

To a solution of 6-bromo-7-methyl-1H-indole-2,3-dione (1 g, 4.77 mmol) in DMF (15 ml) was added sodium hydride (60% dispersion in mineral oil, 333 mg, 8.33 mmol) at room temperature. After stirring at this temperature for 20 minutes, was added 2-bromomethyl-naphthalene (1.94 g, 8.76 mmol) and the reaction mixture was stirred at room temperature overnight. The reaction mixture was then partitioned between water and ethyl acetate. The organic layer was dried over $MgSO_4$, filtered and concentrated under vacuum to give the crude product which was chromatographed on flash silica gel eluting with 10% ethyl acetate in hexane, providing the title compound of the title compound of 2B (1.3 g, 82% yield).

10C. 6-Bromo-7-methyl-1-naphthalen-2-ylmethyl-1,3-dihydro-indol-2-one

6-Bromo-7-methyl-1-naphthalen-2-ylmethyl-1H-indole-2,3-dione (1.04 g, 2.58 mmol) was dissolved in 20 ml of hydrazine hydrate and refluxed for 120 minutes. The reaction mixture was poured into cold water, extracted in ethyl acetate, dried over $MgSO_4$, filtered and concentrated under vacuum to give the crude product. It was chromatographed on flash silica gel eluting with 5% ethyl acetate in hexane to yield the title compound of 2C (0.592 g, 59% yield).

10D. 6-Bromo-7-methyl-1-naphthalen-2-ylmethyl-3,3-bis-pyridin-4-ylmethyl-1,3-dihydro-indol-2-one To a solution of 6-bromo-7-methyl-1-naphthalen-2-ylmethyl-1,3-dihydro-indol-2-one (495.7 mg, 1.36 mmol) in THF (30 ml) was added 4-picolyl chloride hydrochloride (893 mg, 5.45 mmol). The resulting suspension was purged with nitrogen gas for 10 minutes, after which time an aqueous potassium hydroxide (1N, 10.88 ml, degassed for 10 minutes prior to the addition) was added dropwise at room temperature. The dark solution was stirred at room temperature overnight. After removal of THF, the reaction mixture was partitioned between water and ethyl ether. The organic layer was dried over $MgSO_4$, filtered and concentrated under vacuum to give the crude product. It was chromatographed on flash silica gel eluting with ethyl acetate to provide the title compound of 2D (524 mg, 0.956 mmol, 70.3% yield).

C.l. m/z 549.9, 548.1 [M+1].

10E. 4-(7-Methyl-1-naphthalen-2-ylmethyl-2-oxo-3,3-bis-pyridin-4-ylmethyl-2,3-dihydro-1H-indol-6-yl)-benzonitrile To a solution of 6-bromo-7-methyl-1-naphthalen-2-ylmethyl-3,3-bis-pyridin-4-ylmethyl-1,3-dihydro-indol-2-one (200 mg, 0.365 mmol) in 4 ml of toluene and 2.5 ml of EtOH was added tetrakis(triphenylphosphine)palladium (17 mg, 0.015 mmol) under an atmosphere of dry $N_2$, followed by the addition of a solution of aqueous sodium carbonate ($Na_2CO_3$) (77 mg, 0.738 mmol) dissolved in 2 ml of water and 4-cyanobenzene boronic acid (101 mg, 0.686 mmol). The reaction mixture was heated to 100° C. and stirred at this temperature overnight. The reaction mixture was concentrated under vacuum and then partitioned between DCM and saturated aqueous $NaHCO_3$. The organic layer was dried over $MgSO_4$, filtered and concentrated under vacuum to give the crude product. It was chromatographed on silica gel eluting $MeOH/NH_4OH/CHCl_3/(3/0.3/97)$ to give the titled compound of Example 10 (194 mg, 93% yield).

C.l. m/z 571.2 [M+1];

EXAMPLE 11

4-(7-Methyl-1-naphthalen-1-ylmethyl-2-oxo-3,3-bis-pyridin-4-ylmethyl-2,3-dihydro-1H-indol-6-yl)-benzonitrile 11A. 6-Bromo-7-methyl-1-naphthalen-1-ylmethyl-1,3-dihydro-indol-2-one The same procedure was used as that in example 10B, except that 1-iodomethyl-naphthalene (1.85 g, 6.86 mmol) was used in the place of 2-bromomethyl-naphthalene to give the crude title compound of 11A as an orange solid.

11B. 6-Bromo-7-methyl-1-naphthalen-1-ylmethyl-1,3-dihydro-indol-2-one

Following the same procedure as described in example 10C, 6-bromo-7-methyl-1-naphthalen-1-ylmethyl-1,3-dihydro-indol-2-one (2 g, crude) was treated with hydrazine to provide the crude title compound of 11B which was chromatographed on flash silica gel eluting with a gradient of hexane to ethyl acetate/hexane (10% to 20%) to give the title compound of 11B as an orange solid (0.368 g, 48% yield for two steps).

11C. 6-Bromo-7-methyl-1-naphthalen-1-ylmethyl-3,3-bis-pyridin-4-ylmethyl-1,3-dihydro-indol-2-one The same procedure was used as that in example 10D, except that 6-bromo-7-methyl-1-naphthalen-1-ylmethyl-1, 3-dihydro-indol-2-one (0.367 g, 1.00 mmol) was used in the place of 6-bromo-7-methyl-1-naphthalen-2-ylmethyl-1,3-dihydro-indol-2-one to give the title compound of 11C as a white solid (300 mg, 54.7% yield).

11D. 4-(7-Methyl-1-naphthalen-1-ylmethyl-2-oxo-3,3-bis-pyridin-4-ylmethyl-2,3-dihydro-1H-indol-6-yl)-benzonitrile The same procedure was used as that in example 10E, except that 6-bromo-7-methyl-1-naphthalen-1-ylmethyl-3, 3-bis-pyridin-4-ylmethyl-1,3-dihydro-indol-2-one (0.100 g, 0.182 mmol) was used in the place of 6-bromo-7-methyl-1-naphthalen-2-ylmethyl-3,3-bis-pyridin-4-ylmethyl-1,3-dihydro-indol-2-one to give the title compound of 11D as a white solid (45 mg, 43.3% yield).

C.l. m/z 571.2 [M+1].

EXAMPLE 12

4-[6-(4-Cyano-phenyl)-7-methyl-2-oxo-3,3-bis-pyridin-4-ylmethyl-2,3-dihydro-indol-1-ylmethyl]-N,N-dimethyl-benzenesulfonamide 12A. 4-(6-Bromo-7-methyl-2,3-dioxo-2,3-dihydro-indol-1-ylmethyl)-N,N-dimethyl-benzenesulfonamide To a solution of 6-bromo-7-methyl-1H-indole-2,3-dione (2.0 g, 8.33 mmol) in DMF (25 ml) was added potassium carbonate (2.3 g, 16.6 mmol). After stirring at this temperature for 30 minutes, was added 4-bromomethyl-N,N-dimethyl-benzenesulfonamide (3.0 g, 10.83 mmol). The reaction mixture was stirred at room temperature for six hours. It was then partitioned between water and ethyl acetate. The organic layer was dried over $MgSO_4$, filtered and concentrated under vacuum to give the crude product which was chromatographed on flash silica gel eluting with 20% ethyl acetate in hexane, providing the title compound of 12A (0.392 g, 11% yield).

12B. 4-(6-Bromo-7-methyl-2-oxo-2,3-dihydro-indol-1-ylmethyl)-N,N-dimethyl-benzenesulfonamide Following the same procedure as described in example 10C, 4-(6-bromo-7-methyl-2,3-dioxo-2,3-dihydro-indol-1-ylmethyl)-N,N-dimethyl-benzenesulfonamide (0.392 g, 0.895 mmol) was treated with hydrazine to provide the crude title compound of 12B.

C.l. m/z 421/423 [M+1].

12C. 4-(6-Bromo-7-methyl-2-oxo-3,3-bis-pyridin-4-ylmethyl-2,3-dihydro-indol-1-ylmethyl)-N,N-dimethyl-benzenesulfonamide The same procedure was used as that in example 10D, except that 4-(6-bromo-7-methyl-2-oxo-2,3-dihydro-indol-1-ylmethyl)-N,N-dimethyl-benzenesulfonamide (0.100 g, 0.182 mmol) was used in the place of 6-bromo-7-methyl-1-naphthalen-2-ylmethyl-1,3-dihydro-indol-2-one to give the title compound of 12C as a white solid (161 mg, 30% yield for two steps).

12D. 4-[6-(4-Cyano-phenyl)-7-methyl-2-oxo-3,3-bis-pyridin-4-ylmethyl-2,3-dihydro-indol-1-ylmethyl]-N,N-dimethyl-benzenesulfonamide The same procedure was used as that in example 10E, except that 6-bromo-7-methyl-1-naphthalen-1-ylmethyl-3, 3-bis-pyridin-4-ylmethyl-1,3-dihydro-indol-2-one (0.100 g, 0.17 mmol) was used in the place of 6-bromo-7-methyl-1-naphthalen-2-ylmethyl-3,3-bis-pyridin-4-ylmethyl-1,3-dihydro-indol-2-one to give the title compound of 12D as a white solid (15 mg, 14% yield).

C.l. m/z 628.2 [M+1].

EXAMPLE 13

4-[7-Methyl-1-naphthalen-1-ylmethyl-2-oxo-3-(1H-pyrazol-4-ylmethyl)-3-pyridin-4-ylmethyl-2,3-dihydro-1H-indol-6-yl]-benzonitrile 13A. 4-(7-Methyl-1-naphthalen-1-ylmethyl-2-oxo-2,3-dihydro-1H-indol-6-yl)-benzonitrile The same procedure was used as that in example 10E, except that 6-bromo-7-methyl-1-naphthalen-1-ylmethyl-1, 3-dihydro-indol-2-one (11B, 0.800 g, 2.2 mmol) was used in the place of 6-bromo-7-methyl-1-naphthalen-2-ylmethyl-3, 3-bis-pyridin-4-ylmethyl-1,3-dihydro-indol-2-one to give the title compound of 13A as a tan solid (0.85 g, 99% yield) after chromatography eluting with $MeOH/CHCl_3/NH_4OH$ (2/98/0.2).

13B. 4-[7-Methyl-1-naphthalen-1-ylmethyl-2-oxo-3-(1-trityl-1H-pyrazol-4-ylmethylene)-2,3-dihydro-1H-indol-6-yl]-benzonitrile To a suspension of 4-(7-methyl-1-naphthalen-1-ylmethyl-2-oxo-2,3-dihydro-1H-indol-6-yl)-benzonitrile (300 mg, 0.773 mmol) and 1-trityl-1H-pyrazole-4-carbaldehyde (303 mg, 0.928 mmol) in methanol (5 ml) was added pyrrolidine (0.323 ml, 3.87 mmol). The reaction mixture was heated at 70° C. overnight. After cooled to room temperature, the reaction mixture formed a precipitate. The solid was collected and washed with cold methanol to give the title compound of 13B as a bright yellow solid (340 mg, 63.2% yield).

13C. 4-[7-Methyl-1-naphthalen-1-ylmethyl-2-oxo-3-(1H-pyrazol-4-ylmethylene)-2,3-dihydro-1H-indol-6-yl]-benzonitrile To a solution of the title compound of 13B (0.281 g, 0.404 mmol) in TFA (2.5 ml) and DCM (1 ml) was added triethylsilane (97 □l, 0.606 mmol) under an atmosphere of dry $N_2$ and stirred for 5 hour. The reaction mixture was concentrated under vacuum and partitioned between aqueous potassium carbonate and DCM. The organic layer was washed with brine, dried over $Na_2SO_4$, filtered and concentrated under vacuum to give the crude title compound of example 13C.

13D. 4-[7-Methyl-1-naphthalen-1-ylmethyl-2-oxo-3-(1H-pyrazol-4-ylmethyl)-3-pyridin-4-ylmethyl-2,3-dihydro-1H-indol-6-yl]-benzonitrile The title compound of 13C (188 mg, 0.404 mmol) was dissolved in a mixed solvent of methanol (3 ml) and THF (1 ml). The solution was deoxygenated for 15 minutes by bubbling $N_2$ through the reaction mixture. Powdered sodium borohydride ($NaBH_4$, 30 mg, 0.808 mmol) was added. The reaction mixture was stirred for 30 minutes after which time it was concentrated under vacuum to remove methanol. The residue was dissolved in 3 ml of THF. The reaction mixture was deoxygenated for 15 minutes by bubbling $N_2$ through the solution. 1.22 ml of 1 N aqueous KOH, which was deoxygenated prior to the addition, was added to the mixture followed by the hydrochloride salt of picolyl chloride (73 mg, 0.444 mmol). The mixture was stirred at ambient temperature overnight after which time it was partitioned between ethyl acetate and aqueous saturated $NaHCO_3$. The organic extracts were combined, dried over $MgSO_4$, filtered and concentrated under vacuum to give the crude product.

EXAMPLE 14

4-[3,3-Bis-(1H-imidazol-4-ylmethyl)-7-methyl-1-naphthalen-1-ylmethyl-2-oxo-2,3-dihydro-1H-indol-6-yl]-benzonitrile 14A. 4-[7-Methyl-1-naphthalen-1-ylmethyl-2-oxo-3,3-bis-(1-trityl-1H-imidazol-4-ylmethyl)-2,3-dihydro-1H-indol-6-yl]-benzonitrile The title compound of 13A (250 mg, 0.644 mmol) and 4-chloromethyl-1-trityl-1H-imidazole compound (694 mg, 1.93 mmol) were dissolved in 4 ml of anhydrous THF under an atmosphere of dry $N_2$. To this solution was added 95% KHMDS (338 mg, 1.61 mmol) and the reaction mixture was subsequently stirred overnight. The reaction mixture was partitioned between ethyl acetate and aqueous saturated $NaHCO_3$. The organic layer was dried over $MgSO_4$, filtered and concentrated under vacuum to give a pink solid which was chromatographed on flash silica gel eluting with a gradient of ethyl acetate to MeOH in ethyl acetate (10%) to give the title compound of 14A (348 mg, 52% yield).

14B. [3,3-Bis-(1H-imidazol-4-ylmethyl)-7-methyl-1-naphthalen-1-ylmethyl-2-oxo-2,3-dihydro-1H-indol-6-yl]-benzonitrile To a solution of the title compound of example 14A (0.300 g, 0.29 mmol) in TFA (6 ml) and DCM (3 ml) was added triethylsilane (186 □l, 1.16 mmol) followed by addition of ammonia fluoride ($NH_4F$, 0.043 g, 1.16 mmol) under an atmosphere of dry $N_2$ and stirred for 12 hour. The reaction mixture was concentrated under vacuum and partitioned between aqueous potassium carbonate and chloroform. The organic layer was washed with brine, dried over $MgSO_4$, filtered and concentrated under vacuum to give the crude product. It was chromatographed on flash silica gel eluting with $MeOH/CHCl_3/NH_4OH$ (10/89/1) to give the title compound of Example 14 as a white solid (74 mg, 46.6% yield).

C.l. m/z 549.2 [M+1].

EXAMPLE 15

4-[7-Methyl-3,3-bis-(5-methyl-1H-imidazol-4-ylmethyl)-1-naphthalen-1-ylmethyl-2-oxo-2,3-dihydro-1H-indol-6-yl]-benzonitrile 15A. 4-[7-Methyl-3,3-bis-(5-methyl-1-trityl-1H-imidazol-4-ylmethyl)-1-naphthalen-1-ylmethyl-2-oxo-2,3-dihydro-1H-indol-6-yl]-benzonitrile Following the same procedure as described in example 14A, the reaction of the title compound of 13A (0.191 g, 0.49 mmol) and 4-chloromethyl-5-methyl-1-trityl-1H-imidazole (0.55 g, 1.48 mmol) yielded the title compound of 15A (282.2 mg, 71% yield).

C.l. m/z 1061 [M+1].

15B. 4-[7-Methyl-3,3-bis-(5-methyl-1H-imidazol-4-ylmethyl)-1-naphthalen-1-ylmethyl-2-oxo-2,3-dihydro-1H-indol-6-yl]-benzonitrile The same procedure was used as that in example 14B, except that 15A (0.282 g, 0.266 mmol) was used in the place of 14A to give the title compound of Example 15 as a white solid (79.5 mg, 52% yield).

C.l. m/z 577.3 [M+1].

EXAMPLE 16

4-(2-Naphthalen-1-ylmethyl-1,3-dioxo-4,4-bis-pyridin-4-ylmethyl-1,2,3,4-tetrahydro-isoquinolin-7-yl)-benzonitrile 16A. 5-Bromo-2-carboxymethyl-benzoic acid (4-Bromo-phenyl)-acetic acid (20 g, 93 mmol) in thionyl chloride (40 ml) was heated at 850° C. for two hours after which time thionyl chloride was removed under vacuum. The resulting acid chloride was combined with lead thiocyanate ($Pb(SCN)_2$, 30 g, 93 mmol) in benzene (300 ml). The reaction mixture was refluxed for 3 hours. After cooled to room temperature, it was filtered through celite. The filtrate was evaporated to yield an orange liquid. This was then dissolved in carbon disulfide (30 ml) and was added dropwise into a solution of aluminum chloride ($AlCl_3$, 24.7 g, 186 mmol) in carbon disulfide (60 ml) at 0° C. The reaction mixture was heated to reflux for 12 hours. The reaction mixture was cooled to 0° C. and 1N aqueous HCl (200 ml) was added. The resulting orange precipitate was collected and then suspended in ethyl acetate. After filtration obtained an orange solid. This solid was dissolved in 25% aqueous KOH (80 ml). The solution was heated to reflux for 15 hours. After cooling to 0° C., the reaction mixture was adjusted to pH 3 with 6N aqueous HCl. The aqueous solution was extracted with ethyl acetate repeatedly. The combined organic layers were washed with brine, dried over $MgSO_4$ and concentrated under vacuum to provide the title compound of 16A as a yellow solid (12.22 g, 50.7% yield).

16B. 7-Bromo-isochroman-1,3-dione

To the title compound of 16A in acetonitrile ($CH_3CN$, 60 ml) was added N,N'-dicyclohexylcarbodiimide (DCC, 5.8 g, 28.2 mmol). The reaction mixture was stirred at ambient temperature overnight. After filtration, the filtrate was evaporated to give the title compound of 16B as a yellow solid (96.32 g, 98.7% yield).

16C. 7-Bromo-2-naphthalen-1-ylmethyl-4H-isoquinoline-1,3-dione

To a suspension of the title compound of 16B in xylene (20 ml) and dioxane (10 ml) was added 1-naphthlenemethyl amine (0.435 ml, 2.97 mmol). The reaction mixture was heated to 140° C. for 14 hours after which time it was concentrated. The residue was chromatographed on flash silica gel eluting with a gradient of hexane to 10% hexane in ethyl acetate to give the title compound of 16C (230 mg, 40% yield).

C.l. m/z 382, 380 [M+1].

16D. 7-Bromo-2-naphthalen-1-ylmethyl-4,4-bis-pyridin-4-ylmethyl-4H-isoquinoline-1,3-dione The same procedure was used as that in example 10D except that 7-bromo-2-naphthalen-1-ylmethyl-4H-isoquinoline-1,3-dione was used in the place of 6-bromo-7-methyl-1-naphthalen-2-ylmethyl-1,3-dihydro-indol-2-one to give the title compound of 16D as a white solid (51 mg, 21.4% yield).

16E. 4-(2-Naphthalen-1-ylmethyl-1,3-dioxo-4,4-bis-pyridin-4-ylmethyl-1 2,3,4-tetrahydro-isoquinolin-7-yl)-benzaldehyde Following the same procedure as described in example 10E, reaction of the tile compound of 16D (76 mg, 0.135 mmol) and 4-formylphenylboronic acid (30 mg, 0.2 mmol) yielded crude product of the title compound of 16E.

16F. 4-(2-Naphthalen-1-ylmethyl-1,3-dioxo-4,4-bis-pyridin-4-ylmethyl-1,2,3,4-tetrahydro-isoquinolin-7-yl)-benzonitrile The crude product was chromatographed on flash silica gel eluting with $MeOH/CHCl_3/NH_4OH$ (5/95/0.5) to provide the title compound of Example 13D (35 mg, 15% yield).

C.l. m/z 560.1 [M+1].

The title compound of 16E was dissolved in a solution of DCM (1 ml) and ethanol (0.5 ml). To this solution was added hydroxyamine hydrochloride (16 mg, 0.232 mmol). The reaction mixture was stirred at room temperature overnight after which time it was partitioned between aqueous saturated $NaHCO_3$ and DCM. The organic layer was washed with brine, dried over $MgSO_4$, filtered and concentrated under vacuum to give 70 mg (0.12 mmol) of the crude oxime which was dissolved in DCM (1 ml). To this solution were added triethyl amine (0.036 ml, 0.26 mmol) and p-tolylsulfonyl chloride (25 mg, 0.13 mmol). The reaction mixture was stirred overnight after which time it was partitioned between aqueous NaHCO3 and DCM. The organic layer was washed with brine, dried over $MgSO_4$, filtered and concentrated under vacuum to give the crude product. It was chromatographed on flash silica gel eluting with ethyl acetate to give the title compound of Example 16 as a white solid (19 mg, 24% yield from 16D).

C.l. m/z 585.1[M+1].

EXAMPLE 17

4-{1,3-Dioxo-4,4-bis-pyridin-4-ylmethyl-2-[1-(thiophene-2-sulfonyl)-pyrrolidin-3-yl]-1,2,3,4-tetrahydro-isoquinolin-7-yl}-benzonitrile 17A. 3-(7-Bromo-1,3-dioxo-3,4-dihydro-1H-isoquinolin-2-yl)-pyrrolidine-1-carboxylic acid tert-butyl ester The same procedure was used as that in example 16C except 3-amino-pyrrolidine-1-carboxylic acid tert-butyl ester (2 g, 8.33 mmol) was used in the place of 1-naphthlenemethyl amine to give the title compound of 17A as a white solid (1.33 g, 37% yield).

17B. 3-(7-Bromo-1,3-dioxo-4-bis-pyridin-4-ylmethyl-3,4-dihydro-1H-isoquinolin-2-yl)-pyrrolidine-1-carboxylic acid tert-butyl ester The same procedure was used as that in example 10D except that the title compound of 17A (0.096 g, 0.16 mmol) was used in the place of 6-bromo-7-methyl-1-naphthalen-2-ylmethyl-1,3-dihydro-indol-2-one to give the title compound of 17B as a white solid (0.267 g, 17% yield).

C.l. m/z 592.8 [M+1].

17C. 3-[7-(4-Cyano-phenyl)-1,3-dioxo-4,4-bis-pyridin-4-ylmethyl-3,4-dihydro-1H-71 isoquinolin-2-yl]-pyrrolidine-1-carboxylic acid tert-butyl ester.

Following the same procedure as describe in example 10E, reaction of the title compound of 17B (0.267 g, 0.45 mmol) and 4-cyanophenylboronic acid (0.124 g, 0.85 mmol) yielded the title compound of 17C (168 mg, 61% yield).

C.l. m/z 614.3 [M+1];

17D. 4-(1,3-Dioxo-4,4-bis-pyridin-4-ylmethyl-2-pyrrolidin-3-yl-1,2,3,4-tetrahydro-isoquinolin-7-yl)-benzonitrile, hydrochloride To a solution of the title compound of 17C (94 mg, 0.154 mmol) in DCM (2 ml) was added trifluoroacetic acid (0.16 ml) at 0° C. The reaction mixture was stirred at room temperature for 2 hours after which time solvent was removed under vacuum to give the title compound of 17D.

17E. 4-{1,3-Dioxo-4,4-bis-pyridin-4-ylmethyl-2-[1-(thiophene-2-sulfonyl)-pyrrolidin-3-yl]-1,2,3,4-tetrahydro-isoquinolin-7-yl}-benzonitrile To a solution of the title compound of 17D (62 mg, 0.112 mmol) in THF (2 ml) and water (2 ml) was added $NaHCO_3$ (30 mg, 0.36 mmol) followed by addition of a solution of 2-thiophenesulfonyl chloride (0.033 g, 0.18 mmol) in THF (1 ml). The reaction mixture was stirred at room temperature for 15 hours after which time it was poured into 10% aqueous $K_2CO_3$. The organic layer was washed with brine, dried over $MgSO_4$, filtered and concentrated under vacuum to give the crude product. It was chromatographed on flash silica gel eluting with a mixed solvent of $MeOH/CHCl_3/NH_4OH$ (1/99/0.1) to give the title compound of Example 17 as a white solid (18.2 mg, 24.6% yield).

C.l. m/z 585.1[M+1].

What is claimed is:

1. A compound of the formula 1

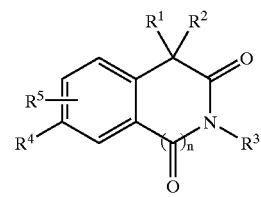

or a pharmaceutically acceptable salt, prodrug, or solvate thereof wherein:

n is 0 or 1;

$R^1$ is $C_1$–$C_3$ alkylpyridyl or $C_1$–$C_3$ alkylimidazolyl;

$R^2$ is selected from the group consisting of $C_1$–$C_{10}$ alkyl, $C_2$–$C_{10}$ alkenyl, $C_2$–$C_{10}$ alkynyl, —$(CH_2)_p(C_6$–$C_{10}$ aryl), and —$(CH_2)_p$(4–10 membered unsaturated heterocyclyl), wherein p is an integer from 0 through 3, and wherein any of said $R^1$ and $R^2$ groups are optionally substituted with 1 to 3 $R^6$ groups;

$R^3$ is —$(CH_2)_m$(1- or 2-adamantyl), —$C_1$–$C_{10}$ alkyl, —$C_2$–$C_{10}$ alkenyl, —$C_2$–$C_{10}$ alkynyl, —$(CH_2)_m$ ($C_6$–$C_{10}$ aryl),

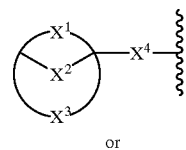

or

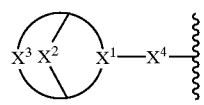

$X^1$, $X^2$, and $X^3$ are each independently $C_1$–$C_7$ alkylene optionally containing 1 or 2 carbon-carbon double bonds, $X^4$ is a bond or $C_1$–$C_7$ alkylene optionally containing 1 or 2 carbon-carbon double or triple bonds, and, in formula (1b), the $X^4$ moiety is attached to the $X^1$ moiety at any available carbon in the $X^1$ moiety, and each of the foregoing $R^3$ groups are substituted with an $R^5$ group and optionally with 1 to 4 $R^6$ groups;

or $R^3$ is —$(CH_2)_tSO_2R^9$, —$(CH_2)_tC(O)R^9$, or —$(CH_2)_m$(4–10 membered heterocyclyl) optionally substituted with 1 to 5 $R^6$ groups;

m, in the aforementioned $R^3$ groups, is independently an integer from 0 through 6 and t is independently an integer from 1 through 5;

$R^4$ is $C_6$–$C_{10}$ aryl or 4–10 membered heterocyclyl, each of said $R^4$ groups being optionally substituted by 1 to 3 $R^6$ groups;

each $R^5$ is independently selected from halo, $C_1$–$C_6$ alkyl optionally substituted by 1 to 3 halo, nitro, cyano, —OR$^9$, —C(O)R$^9$, —SR$^9$, —SO$_2$R$^9$, —SO$_3$H, —S(O)R$^9$, —NR$^7$R$^8$, —CH=NOR$^7$, —C(O)OR$^9$, —OC(O)R$^9$, —SO$_2$NR$^9$R$^8$, —C(O)NR$^9$R$^8$, —NR$^8$C(O)R$^9$, —OC(O)NR$^9$R$^8$, —C(O)ONR$^7$R$^9$, —NR$^8$C(O)NR$^9$R$^8$, —NR$^8$C(O)O(C$_1$–C$_4$ alkyl), —C(NR$^8$)NR$^9$R$^8$, —C(NCN)NR$^9$R$^8$, —C(NCN)S(C$_1$–C$_4$ alkyl or C$_1$–C$_4$ haloalkyl), —NR$^8$C(NCN)S(C$_1$–C$_4$ alkyl or C$_1$–C$_4$ haloalkyl), —NR$^8$C(NCN)NR$^7$R$^8$, —NR$^8$SO$_2$(C$_1$–C$_4$ alkyl or C$_1$–C$_4$ haloalkyl), —NR$^8$C(O)C(O)R$^8$, —NR$^8$C(O)C(O)NR$^9$R$^8$, —P(O)(OR$^7$)$_2$, and —CH$_2$)$_q$ (4–10 membered heterocyclyl), q is an integer from 0 through 3, and the alkyl and heterocyclyl moieties of the foregoing R$^5$ groups are optionally substituted by 1 to 3 R$^{10}$ groups;

each R$^6$ is independently selected from R$^5$, C$_2$–C$_{10}$ alkenyl, C$_2$–C$_{10}$ alkynyl and —(CH$_2$)$_t$(C$_6$–C$_{10}$ aryl) optionally substituted with 1 to 3 R$^{10}$ groups, t being an integer from 0 through 3;

each R$^7$ is independently hydrogen or C$_1$–C$_4$ alkyl optionally substituted by 1 to 3 halo;

each R$^8$ is independently R$^7$ or —OR$^7$;

each R$^9$ is independently selected from hydrogen, C$_1$–C$_6$ alkyl, —(CH$_2$)$_q$(C$_6$–C$_{10}$ aryl) and —(CH$_2$)$_q$ (4–10 membered heterocyclyl), said R$^9$ groups, except H, are optionally substituted with 1 to 3 R$^{10}$ groups, and each q is independently an integer from 0 through 3; and each R$^{10}$ is independently selected from halo, nitro, cyano, C$_1$–C$_6$ alkyl, C$_1$–C$_6$ haloalkyl, C$_1$–C$_6$ haloalkoxy, —C(O)O(C$_1$–C$_6$ alkyl), and C$_6$–C$_{10}$ aryl.

2. The compound according to claim 1, wherein each p in R$^2$ is independently an integer from 1 to 3.

3. The compound according to claim 2, wherein p is 1.

4. The compound according to claim 1, wherein R$^2$ is —(CH$_2$)$_p$(4–10 membered unsaturated heterocyclyl) optionally substituted with 1 to 3 R$^6$ groups.

5. The compound according to claim 4, wherein R$^2$ is a —(CH$_2$)$_p$(5 or 6 membered unsaturated heterocyclyl).

6. The compound according to claim 5, wherein said heterocyclyl is imidazolyl or pyridinyl.

7. The compound according to claim 1, wherein R$^1$ and R$^2$ are independently 4-imidazolylmethyl, 3-pyridinylmethyl, or 4-pyridinylmethyl.

8. The compound according to claim 1, wherein R$^2$ is a C$_1$–C$_{10}$ alkyl substituted by one R$^6$ group.

9. The compound according to claim 8, wherein the R$^6$ group is —SR$^9$.

10. The compound according to claim 1 wherein R$^3$ is —CH$_2$)$_m$(1- or 2-adamantyl) or —(CH$_2$)$_m$(C$_6$–C$_{10}$ aryl), wherein the aryl is optionally substituted with 1 to 5 R$^6$ groups and m is an integer 1.

11. The compound according to claim 10 wherein the aryl group is phenyl or naphthyl and R$^6$ is R$^5$, wherein R$^5$ is —SO$_2$R$^9$, —SO$_2$NR$^9$R$^8$, or —C(O)OR$^9$.

12. The compound according to claim 11 wherein said R$^5$ is —SO$_2$NR$^9$R$^8$.

13. The compound according to claim 1 wherein R$^4$ is C$_6$–C$_{10}$ aryl substituted by R$^6$.

14. The compound according to claim 13 wherein R$^6$ is cyano.

15. The compound according to claim 1 wherein R$^4$ is C$_6$–C$_{10}$ aryl substituted by R$^6$, wherein the R$^6$ is halo or formyl, provided that when the R$^6$ is bromo, then R$^3$ is substituted by R$^5$, wherein R$^5$ is sulfonamide.

16. A compound selected from the group consisting of:
4-[6-(4-Cyano-phenyl)-3,3-bis-(1H-imidazol-4-ylmethyl)-2-oxo-2,3-dihydro-indol-1-ylmethyl]-N,N-dimethyl-benzenesulfonamide;
4-[3,3-Bis-(3H-imidazol-4-ylmethyl)-1-naphthalen-1-ylmethyl-2-oxo-2,3-dihydro-1H-indol-6-yl]-benzonitrile;
4-[1-Adamantan-1-ylmethyl-3-(1H-imidazol-4-ylmethyl)-3-(3H-imidazol-4-ylmethyl)-2-oxo-2,3-dihydro-1H-indol-6-yl]-benzonitrile;
4-[3-(1H-Imidazol-4-ylmethyl)-3-(3H-imidazol-4-ylmethyl)-2-oxo-1-quinolin-4-ylmethyl-2,3-dihydro-1H-indol-6-yl]-benzonitrile;
4-[6-(4-Formyl-phenyl)-2-oxo-3,3-bis-pyridin-4-ylmethyl-2,3-dihydro-indol-1-ylmethyl]-N,N-dimethyl-benzenesulfonamide;
4-[6-(4-Cyano-phenyl)-2-oxo-3,3-bis-pyridin-4-ylmethyl-2,3-dihydro-indol-1-ylmethyl]-N,N-dimethyl-benzenesulfonamide;
4-(1-Naphthalen-1-ylmethyl-2-oxo-3,3-bis-pyridin-4-ylmethyl-2,3-dihydro-1H-indol-6-yl)-benzonitrile;
4-(2-Oxo-3,3-bis-pyridin-4-ylmethyl-1-quinolin-4-ylmethyl-2,3-dihydro-1H-indol-6-yl)-benzonitrile;
4-[1-Adamantan-1-ylmethyl-3,3-bis-(3-methyl-3H-imidazol-4-ylmethyl)-2-oxo-2,3-dihydro-1H-indol-6-yl]-benzonitrile;
4-(7-Methyl-1-naphthalen-2-ylmethyl-2-oxo-3,3-bis-pyridin-4-ylmethyl-2,3-dihydro-1H-indol-6-yl)-benzonitrile;
4-(7-Methyl-1-naphthalen-1-ylmethyl-2-oxo-3,3-bis-pyridin-4-ylmethyl-2,3-dihydro-1H-indol-6-yl)-benzonitrile;
4-[6-(4-Cyano-phenyl)-7-methyl-2-oxo-3,3-bis-pyridin-4-ylmethyl-2,3-dihydro-indol-1-ylmethyl]-N,N-dimethyl-benzenesulfonamide;
4-[7-Methyl-1-naphthalen-1-ylmethyl-2-oxo-3-(1H-pyrazol-4-ylmethyl)-3-pyridin-4-ylmethyl-2,3-dihydro-1H-indol-6-yl]-benzonitrile;
4-[3,3-Bis-(1H-imidazol-4-ylmethyl)-7-methyl-1-naphthalen-1-ylmethyl-2-oxo-2,3-dihydro-1H-indol-6-yl]-benzonitrile;
4-[7-Methyl-3,3-bis-(5-methyl-1H-imidazol-4-ylmethyl)-1-naphthalen-1-ylmethyl-2-oxo-2,3-dihydro-1H-indol-6-yl]-benzonitrile;
4-(2-Naphthalen-1-ylmethyl-1,3-dioxo-4,4-bis-pyridin-4-ylmethyl-1,2,3,4-tetrahydro-isoquinolin-7-yl)-benzonitrile; and
4-{1,3-Dioxo-4,4-bis-pyridin-4-ylmethyl-2-[1-(thiophene-2-sulfonyl)-pyrrolidin-3-yl]-1,2,3,4-tetrahydro-isoquinolin-7-yl}-benzonitrile;

and the pharmaceutically acceptable salts, prodrugs, and solvates of the foregoing compounds.

17. A method for the inhibition of abnormal cell growth in a mammal comprising administering to said mammal in need thereof an amount of a compound according to claim 1 that is effective in inhibiting farnesyl protein transferase.

18. The method according to claim 17 wherein said cell is a tumor cell.

19. A pharmaceutical composition for the inhibition of abnormal cell growth in a mammal which comprises an amount of a compound according to claim 1 that is effective in inhibiting farnesyl protein transferase and a pharmaceutically acceptable carrier.

20. A pharmaceutical composition according to claim 19 wherein said cell is a tumor cell.

21. A method of preparing a compound of formula 1:

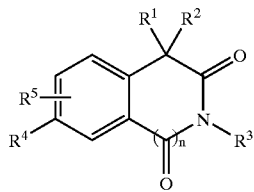

or a pharmaceutically acceptable salt, prodrug, or solvate thereof wherein:

n is 0 or 1;

$R^1$ and $R^2$ are $C_1$–$C_3$ alkylpyridyl or $C_1$–$C_3$ alkylimidazolyl;

$R^3$ is —$(CH_2)_m$(1- or 2-adamantyl), —$C_1$–$C_{10}$ alkyl, —$C_2$–$C_{10}$ alkenyl, —$C_2$–$C_{10}$ alkynyl, —$(CH_2)_m$($C_6$–$C_{10}$ aryl),

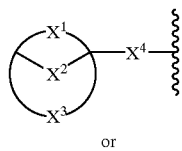 (1a)

or

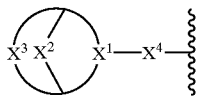 (1b)

$X^1$, $X^2$, and $X^3$ are each independently $C_1$–$C_7$ alkylene optionally containing 1 or 2 carbon-carbon double bonds, $X^4$ is a bond or $C_1$–$C_7$ alkylene optionally containing 1 or 2 carbon-carbon double or triple bonds, and, in formula (1b), the $X^4$ moiety is attached to the $X^1$ moiety at any available carbon in the $X^1$ moiety, and each of the foregoing $R^3$ groups are substituted with an $R^5$ group and optionally with 1 to 4 $R^6$ groups;

or $R^3$ is —$(CH_2)_t SO_2 R^9$, —$(CH_2)_t C(O)R^9$, or —$(CH_2)_m$ (4–10 membered heterocyclyl) optionally substituted with 1 to 5 $R^6$ groups;

m, in the aforementioned $R^3$ groups, is independently an integer from 0 through 6 and t is independently an integer from 1 through 5;

$R^4$ is $C_6$–$C_{10}$ aryl or 4–10 membered heterocyclyl, each of said $R^4$ groups being optionally substituted by 1 to 3 $R^6$ groups;

each $R^5$ is independently selected from halo, $C_1$–$C_6$ alkyl optionally substituted by 1 to 3 halo, nitro, cyano, —$OR^9$, —$C(O)R^9$, —$SR^9$, —$SO_2R^9$, —$SO_3H$, —$S(O)R^9$, —$NR^7R^8$, —$CH=NOR^7$, —$C(O)OR^9$, —$OC(O)R^9$, —$SO_2NR^9R^8$, —$C(O)NR^9R^8$, —$NR^8C(O)R^9$, —$OC(O)NR^9R^8$, —$C(O)ONR^7R^9$, —$NR^8C(O)NR^9R^8$, —$NR^8C(O)O(C_1$–$C_4$ alkyl), —$C(NR^8)NR^9R^8$, —$C(NCN)NR^9R^8$, —$C(NCN)S(C_1$–$C_4$ alkyl or $C_1$–$C_4$ haloalkyl), —$NR^8C(NCN)S(C_1$–$C_4$ alkyl or $C_1$–$C_4$ haloalkyl), —$NR^8C(NCN)NR^7R^8$, —$NR^8SO_2(C_1$–$C_4$ alkyl or $C_1$–$C_4$ haloalkyl), —$NR^8C(O)C(O)R^8$, —$NR^8C(O)C(O)NR^9R^8$, —$P(O)(OR^7)_2$, and —$(CH_2)_q$ (4–10 membered heterocyclyl), q is an integer from 0 through 3, and the alkyl and heterocyclyl moieties of the foregoing $R^5$ groups are optionally substituted by 1 to 3 $R^{10}$ groups;

each $R^6$ is independently selected from $R^5$, $C_2$–$C_{10}$ alkenyl, $C_2$–$C_{10}$ alkynyl and —$(CH_2)_t(C_6$–$C_{10}$ aryl) optionally substituted with 1 to 3 $R^{10}$ groups, t being an integer from 0 through 3;

each $R^7$ is independently hydrogen or $C_1$–$C_4$ alkyl optionally substituted by 1 to 3 halo;

each $R^8$ is independently $R^7$ or —$OR^7$;

each $R^9$ is independently selected from hydrogen, $C_1$–$C_6$ alkyl, —$(CH_2)_q(C_6$–$C_{10}$ aryl) and —$(CH_2)_q$ (4–10 membered heterocyclyl), said $R^9$ groups, except H, are optionally substituted with 1 to 3 $R^{10}$ groups, and each q is independently an integer from 0 through 3; and each $R^{10}$ is independently selected from halo, nitro, cyano, $C_1$–$C_6$ alkyl, $C_1$–$C_6$ haloalkyl, $C_1$–$C_6$ haloalkoxy, —$C(O)O(C_1$–$C_6$ alkyl), and $C_6$–$C_{10}$ aryl;

which comprises treating a compound of formula 2:

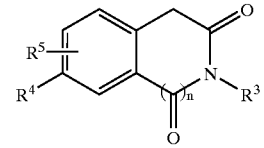

wherein the substituents are as described above;

with a compound of formula RW, wherein W is a leaving group and R is $C_1$–$C_3$ alkylpyridyl or $C_1$–$C_3$ alkylimidazolyl.

* * * * *